United States Patent [19]
Suri et al.

[11] Patent Number: 5,559,007
[45] Date of Patent: Sep. 24, 1996

[54] BACTERIAL SHUTTLE VECTORS

[76] Inventors: Bruno Suri, Spalentorweg 4; Albert Schmitz, Gasstrasse 53, both of Basel, Switzerland

[21] Appl. No.: 186,222

[22] Filed: Jan. 21, 1994

Related U.S. Application Data

[63] Continuation of Ser. No. 672,205, Mar. 19, 1991, abandoned.

[30] Foreign Application Priority Data

Mar. 22, 1990 [GB] United Kingdom ............... 9006400

[51] Int. Cl.$^6$ ............................ C12N 15/70; C12N 15/74
[52] U.S. Cl. ................... 435/69.1; 435/69.7; 435/69.8; 435/172.3; 435/252.3; 435/252.31; 435/252.33; 435/853; 536/23.1; 536/23.4; 536/23.7; 536/24.1
[58] Field of Search .................... 435/69.1, 69.7, 435/69.8, 172.3, 320.1, 240.1, 252.3, 252.31, 252.33, 254.11, 240.1, 853; 536/23.1, 23.2, 23.4, 23.7, 24.1

[56] References Cited

FOREIGN PATENT DOCUMENTS

| | | |
|---|---|---|
| 0228726 | 7/1987 | European Pat. Off. . |
| 316677 | 5/1989 | European Pat. Off. . |
| 0455280 | 11/1991 | European Pat. Off. . |
| WO85/03945 | 9/1985 | WIPO . |

OTHER PUBLICATIONS

Maniatis et al., Molecular Cloning: A Laboratory Manual, Cold Spring Harbor Laboratory, Cold Spring Harbor, NY 1982, pp. 429, 430 & 433 (422 & 249 previously provided).
Maniatis et al. Molecular Cloning, CSH 1982 pp. 3–4, 249 & 422.
Chassy, FEMS Microbiology Reviews, vol. 46, pp. 297–312 (1987).
Gasson et al., FEMS Microbiology Reviews, vol. 30, pp. 193–196 (1985).
De Vos, FEMS Microbiology Reviews, vol. 46, pp. 281–295 (1987).
Jos et al., Applied and Environmental Microbiology, vol. 50, pp. 540–542 (1985).
Harlander et al., Applied and Environmental Microbiology, vol. 48, pp. 347–351 (1984).
Davies et al., J. Appl. Bacteriol., vol. 51, pp. 325–337 (1981).
Aschen et al., Gene, vol. 45, pp. 45–49 (1986).
Gasson, J. Bacteriol., vol. 154, pp. 1–9 (1983).
Macrina et al., Gene, vol. 19, pp. 345–353 (1982).
Simmons et al., J. Dairy Sci., 71:83 (1988), Abstract D64.
De Vos et al., *J. Dairy Sci.*, 72:3398–3405 (1989).
De Vos, Netherlands Milk and Dairy Journal, 40:141–154 (1986).
van Asseldonk et al., Gene, 95:155–160 (1990).

*Primary Examiner*—John L. LeGuyader
*Attorney, Agent, or Firm*—James Scott Elmer

[57] ABSTRACT

The invention relates to the field of genetic engineering and provides novel DNA molecules which comprise multifunctional origins of replication and/or a DNA sequence coding for the most abundant protein in the supernatant of cultures of Lactococcus Spec., named Major Secretion Product (MSP), for its signal peptide and/or the promoter of the MSP gene. The novel DNA molecules are used for the production of novel shuttle vectors for cloning of DNA in at least *E. coli* and Lactococcus spec. or novel vectors for the expression of homologous or heterologous genes and the production of secreted gene products in gram positive bacteria such as Lactococcus spec. and Bacillus Spec.

49 Claims, 3 Drawing Sheets

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 1920 base pairs
( B ) TYPE: nucleic acid
( C ) STRANDEDNESS: double
( D ) TOPOLOGY: linear ( i i ) MOLECULE TYPE: DNA (genomic)

( v ) ORIGINAL SOURCE:
( A ) ORGANISM: Lactococcus lactis LM0230
( C ) INDIVIDUAL ISOLATE: Major Secretion Product (MSP) Gene ( v i i ) IMMEDIATE SOURCE:
( B ) CLONE: pUCRS ( i x ) FEATURE:
  ( A ) NAME/KEY: CDS
  ( B ) LOCATION: 411..1793

( x i ) SEQUENCE DESCRIPTION: SEQ ID NO:1:

| | | | | | | |
|---|---|---|---|---|---|---|
| TTTAGGTATT | TACGGAATTG | CGACCTTATT | GTTCCCACTT | ATTGCTCTTT | TTGTATATAA | 60 |
| TATACAAATA | ACTATATTTA | CTAATCGCTG | ACAAGGCTT | TTTACAACAA | TTATTATTGT | 120 |
| GACCGCTTTT | GAAGTTTTA | GTGCAATCAT | TATGACAGCT | TTTGGATTTG | CCCAACTTCA | 180 |
| GTTTATCAAA | TTTGTTGTTT | ACCAGTTAGC | GCCTACACTT | TGCTCAATA | TTATCTTAGC | 240 |
| TGTAGCCTTA | CAATTCCCTT | TAGAAATCTT | TTACAGATTA | AAGAAAGTC | ATGTAAGATA | 300 |
| CAATTAGAAA | GTGTTTTGTA | ATCATAAAGA | AATATTAAGG | TGGGGTAGGA | ATAGTATAAT | 360 |
| ATGTTTATTC | AACCGAACTT | AATGGGAGGA | AAAATTAAAA | AAGAACAGTT | ATG AAA | 416 |
| | | | | | Met Lys | |
| | | | | | 1 | |

```
AAA  AAG  ATT  ATC  TCA  GCT  ATT  TTA  ATG  TCT  ACA  GTG  ATA  CTT  TCT  GCT     464
Lys  Lys  Ile  Ile  Ser  Ala  Ile  Leu  Met  Ser  Thr  Val  Ile  Leu  Ser  Ala
          5                        10                       15

GCA  GCC  CCG  TTG  TCA  GGT  GTT  TAC  GCT  GAC  ACA  AAC  TCA  GAT  ATT  GCT     512
Ala  Ala  Pro  Leu  Ser  Gly  Val  Tyr  Ala  Asp  Thr  Asn  Ser  Asp  Ile  Ala
     20                        25                       30

AAA  CAA  GAT  GCG  ACA  ATT  TCA  AGC  GCG  CAA  TCT  GCT  AAA  GCA  CAA  GCA     560
Lys  Gln  Asp  Ala  Thr  Ile  Ser  Ser  Ala  Gln  Ser  Ala  Lys  Ala  Gln  Ala
35                       40                       45                       50

CAA  GCA  CAA  GTT  GAT  AGC  TTG  CAA  TCA  AAA  GTT  GAC  AGC  TTA  CAA  CAA     608
Gln  Ala  Gln  Val  Asp  Ser  Leu  Gln  Ser  Lys  Val  Asp  Ser  Leu  Gln  Gln
               55                       60                       65

AAG  CAA  ACA  AGT  ACT  AAA  GCA  CAA  ATC  GCT  AAA  ATC  GAA  AGC  GAA  CGT     656
Lys  Gln  Thr  Ser  Thr  Lys  Ala  Gln  Ile  Ala  Lys  Ile  Glu  Ser  Glu  Arg
                    70                       75                       80

AAA  GCA  CTT  AAT  GCT  CAA  ATT  GCT  ACT  TTG  AAC  GAA  AGT  ATC  AAA  GAA     704
Lys  Ala  Leu  Asn  Ala  Gln  Ile  Ala  Thr  Leu  Asn  Glu  Ser  Ile  Lys  Glu
               85                       90                       95

CGT  ACA  AAG  ACA  TTG  GAA  GCT  CAA  GCA  CGT  AGT  GCT  CAA  GTT  AAC  AGC     752
Arg  Thr  Lys  Thr  Leu  Glu  Ala  Gln  Ala  Arg  Ser  Ala  Gln  Val  Asn  Ser
     100                      105                      110

TCA  GCA  ACA  AAT  TAT  ATG  GAT  GCT  GTT  GTT  AAT  TCA  AAA  TCT  TTG  ACA     800
Ser  Ala  Thr  Asn  Tyr  Met  Asp  Ala  Val  Val  Asn  Ser  Lys  Ser  Leu  Thr
115                      120                      125                      130

GAT  GTT  ATT  CAA  AAA  GTA  ACA  GCT  ATT  GCT  ACT  GTT  TCT  AGT  GCC  AAC     848
Asp  Val  Ile  Gln  Lys  Val  Thr  Ala  Ile  Ala  Thr  Val  Ser  Ser  Ala  Asn
               135                      140                      145

AAA  CAA  ATG  TTG  GAA  CAA  CAA  GAA  AAA  GAG  CAA  AAA  GAG  CTT  AGC  CAA     896
Lys  Gln  Met  Leu  Glu  Gln  Gln  Glu  Lys  Glu  Gln  Lys  Glu  Leu  Ser  Gln
               150                      155                      160

AAG  TCA  GAA  ACT  GTT  AAA  AAG  AAC  TAC  AAC  CAG  TTC  GTT  TCT  CTT  TCA     944
Lys  Ser  Glu  Thr  Val  Lys  Lys  Asn  Tyr  Asn  Gln  Phe  Val  Ser  Leu  Ser
     165                      170                      175

CAA  AGT  TTG  GAT  TCT  CAA  GCT  CAA  GAA  TTG  ACT  TCA  CAA  CAA  GCT  GAA     992
Gln  Ser  Leu  Asp  Ser  Gln  Ala  Gln  Glu  Leu  Thr  Ser  Gln  Gln  Ala  Glu
180                      185                      190

CTC  AAA  GTT  GCG  ACT  TTG  AAC  TAT  CAA  GCA  ACA  ATT  GCA  ACT  GCG  CAA    1040
Leu  Lys  Val  Ala  Thr  Leu  Asn  Tyr  Gln  Ala  Thr  Ile  Ala  Thr  Ala  Gln
195                      200                      205                      210

GAT  AAA  AAA  CAA  GCT  TTA  TTA  GAT  GAA  AAA  GCA  GCT  GCA  GAA  AAA  GCA    1088
Asp  Lys  Lys  Gln  Ala  Leu  Leu  Asp  Glu  Lys  Ala  Ala  Ala  Glu  Lys  Ala
               215                      220                      225

GCT  CAA  GAA  GCA  GCT  AAA  AAA  CAA  GCG  GCT  TAT  GAA  GCT  CAA  CAA  AAA    1136
Ala  Gln  Glu  Ala  Ala  Lys  Lys  Gln  Ala  Ala  Tyr  Glu  Ala  Gln  Gln  Lys
```

|  |  |  |  |  |  |  |  |  |  |  |  |  |  |  |  |
|---|---|---|---|---|---|---|---|---|---|---|---|---|---|---|---|
|  |  |  | 230 |  |  |  | 235 |  |  |  | 240 |  |  |  |  |
| GAA | GCA | GCA | CAA | GCA | CAA | GCA | GCT | TCA | ACA | GCA | GCA | ACT | GCT | AAA | GCT | 1184 |
| Glu | Ala | Ala | Gln | Ala | Gln | Ala | Ala | Ser | Thr | Ala | Ala | Thr | Ala | Lys | Ala |  |
|  |  | 245 |  |  |  |  | 250 |  |  |  |  | 255 |  |  |  |  |
| GTA | GAA | GCA | GCA | ACT | TCA | TCA | GCT | TCT | GCT | TCA | TCT | AGT | CAA | GCT | CCA | 1232 |
| Val | Glu | Ala | Ala | Thr | Ser | Ser | Ala | Ser | Ala | Ser | Ser | Ser | Gln | Ala | Pro |  |
|  | 260 |  |  |  |  | 265 |  |  |  |  | 270 |  |  |  |  |  |
| CAA | GTA | AGT | ACA | AGC | ACT | GAT | AAT | ACA | ACA | TCA | AAT | GCT | AGT | GCC | TCA | 1280 |
| Gln | Val | Ser | Thr | Ser | Thr | Asp | Asn | Thr | Thr | Ser | Asn | Ala | Ser | Ala | Ser |  |
| 275 |  |  |  |  | 280 |  |  |  |  | 285 |  |  |  |  | 290 |  |
| AAC | AGT | TCT | AAT | AGT | TCA | TCA | AAC | TCA | AGT | TCA | AGT | TCT | AGC | AGT | TCA | 1328 |
| Asn | Ser | Ser | Asn | Ser | Ser | Ser | Asn | Ser | Ser | Ser | Ser | Ser | Ser | Ser | Ser |  |
|  |  |  |  | 295 |  |  |  |  | 300 |  |  |  |  | 305 |  |  |
| TCA | AGC | TCA | AGC | TCA | AGC | TCA | AGT | AAT | TCT | AAT | GCT | GGT | GGG | AAT | ACA | 1376 |
| Ser | Ser | Ser | Ser | Ser | Ser | Ser | Ser | Asn | Ser | Asn | Ala | Gly | Gly | Asn | Thr |  |
|  |  |  | 310 |  |  |  |  | 315 |  |  |  |  | 320 |  |  |  |
| AAT | TCA | GGC | ACT | AGT | ACT | GGA | AAT | ACT | GGA | GGA | ACA | ACT | ACT | GGT | GGT | 1424 |
| Asn | Ser | Gly | Thr | Ser | Thr | Gly | Asn | Thr | Gly | Gly | Thr | Thr | Thr | Gly | Gly |  |
|  |  | 325 |  |  |  |  | 330 |  |  |  |  | 335 |  |  |  |  |
| AGC | GGT | ATA | AAT | AGT | TCA | CCA | ATT | GGA | AAT | CCT | TAT | GCT | GTT | GGT | GGA | 1472 |
| Ser | Gly | Ile | Asn | Ser | Ser | Pro | Ile | Gly | Asn | Pro | Tyr | Ala | Val | Gly | Gly |  |
|  | 340 |  |  |  |  | 345 |  |  |  |  | 350 |  |  |  |  |  |
| TGT | ACT | GAC | TAT | GTA | TGG | CAA | TAC | TTT | GCT | GCA | CAA | GGA | ATT | TAT | ATC | 1520 |
| Cys | Thr | Asp | Tyr | Val | Trp | Gln | Tyr | Phe | Ala | Ala | Gln | Gly | Ile | Tyr | Ile |  |
| 355 |  |  |  |  | 360 |  |  |  |  | 365 |  |  |  |  | 370 |  |
| AGA | AAT | ATC | ATG | CCT | GGT | AAT | GGT | GGA | CAA | TGG | GCT | TCT | AAT | GGA | CCT | 1568 |
| Arg | Asn | Ile | Met | Pro | Gly | Asn | Gly | Gly | Gln | Trp | Ala | Ser | Asn | Gly | Pro |  |
|  |  |  |  | 375 |  |  |  |  | 380 |  |  |  |  | 385 |  |  |
| GCC | CAA | GGC | GTG | CTC | CAT | GTT | GTA | GGA | GCT | GCT | CCT | GGT | GTT | ATC | GCA | 1616 |
| Ala | Gln | Gly | Val | Leu | His | Val | Val | Gly | Ala | Ala | Pro | Gly | Val | Ile | Ala |  |
|  |  |  | 390 |  |  |  |  | 395 |  |  |  |  | 400 |  |  |  |
| TCA | AGC | TTC | TCA | GCT | GAT | TTT | GTT | GGA | TAT | GCA | AAC | TCA | CCT | TAC | GGT | 1664 |
| Ser | Ser | Phe | Ser | Ala | Asp | Phe | Val | Gly | Tyr | Ala | Asn | Ser | Pro | Tyr | Gly |  |
|  |  | 405 |  |  |  |  | 410 |  |  |  |  | 415 |  |  |  |  |
| CAC | GTA | GCT | ATT | GTA | AAA | TCA | GTT | AAT | TCA | GAT | GGT | ACA | ATT | ACT | ATC | 1712 |
| His | Val | Ala | Ile | Val | Lys | Ser | Val | Asn | Ser | Asp | Gly | Thr | Ile | Thr | Ile |  |
|  | 420 |  |  |  |  | 425 |  |  |  |  | 430 |  |  |  |  |  |
| AAA | GAA | GGC | GGA | TAT | GGT | ACA | ACT | TGG | TGG | GGA | CAT | GAA | CGT | ACT | GTA | 1760 |
| Lys | Glu | Gly | Gly | Tyr | Gly | Thr | Thr | Trp | Trp | Gly | His | Glu | Arg | Thr | Val |  |
| 435 |  |  |  |  | 440 |  |  |  |  | 445 |  |  |  |  | 450 |  |
| AGT | GCG | TCT | GGT | GTT | ACT | TTC | TTG | ATG | CCA | AAC | TAGAAAAAG | TCTTAATAAA |  |  |  | 1813 |
| Ser | Ala | Ser | Gly | Val | Thr | Phe | Leu | Met | Pro | Asn |  |  |  |  |  |  |
|  |  |  |  | 455 |  |  |  |  | 460 |  |  |  |  |  |  |  |
| TAAAAAATAG | TGGTTTGATA | GTGGGGAATA | ATTTTCCTTC | TGTCAAATCA | TTTTTTATTA |  |  |  |  |  |  |  |  |  |  | 1873 |
| TTGTGGTATA | ATAATAAGGA | AAAATGATAA | GGGGATAGAT | ACAAATG |  |  |  |  |  |  |  |  |  |  |  | 1920 |

( 2 ) INFORMATION FOR SEQ ID NO:2:

( i ) SEQUENCE CHARACTERISTICS:
    ( A ) LENGTH: 461 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

| Met | Lys | Lys | Lys | Ile | Ile | Ser | Ala | Ile | Leu | Met | Ser | Thr | Val | Ile | Leu |
|---|---|---|---|---|---|---|---|---|---|---|---|---|---|---|---|
| 1 |  |  |  | 5 |  |  |  |  | 10 |  |  |  |  | 15 |  |

| Ser | Ala | Ala | Ala | Pro | Leu | Ser | Gly | Val | Tyr | Ala | Asp | Thr | Asn | Ser | Asp |
|---|---|---|---|---|---|---|---|---|---|---|---|---|---|---|---|
|  |  |  | 20 |  |  |  |  | 25 |  |  |  |  | 30 |  |  |

```
Ile Ala Lys Gln Asp Ala Thr Ile Ser Ser Ala Gln Ser Ala Lys Ala
         35                  40                  45

Gln Ala Gln Ala Gln Val Asp Ser Leu Gln Ser Lys Val Asp Ser Leu
     50                  55                  60

Gln Gln Lys Gln Thr Ser Thr Lys Ala Gln Ile Ala Lys Ile Glu Ser
 65                  70                  75                  80

Glu Arg Lys Ala Leu Asn Ala Gln Ile Ala Thr Leu Asn Glu Ser Ile
                 85                  90                  95

Lys Glu Arg Thr Lys Thr Leu Glu Ala Gln Ala Arg Ser Ala Gln Val
             100                 105                 110

Asn Ser Ser Ala Thr Asn Tyr Met Asp Ala Val Val Asn Ser Lys Ser
             115                 120                 125

Leu Thr Asp Val Ile Gln Lys Val Thr Ala Ile Ala Thr Val Ser Ser
         130                 135                 140

Ala Asn Lys Gln Met Leu Glu Gln Gln Glu Lys Glu Gln Lys Glu Leu
145                 150                 155                 160

Ser Gln Lys Ser Glu Thr Val Lys Lys Asn Tyr Asn Gln Phe Val Ser
                 165                 170                 175

Leu Ser Gln Ser Leu Asp Ser Gln Ala Gln Glu Leu Thr Ser Gln Gln
             180                 185                 190

Ala Glu Leu Lys Val Ala Thr Leu Asn Tyr Gln Ala Thr Ile Ala Thr
         195                 200                 205

Ala Gln Asp Lys Lys Gln Ala Leu Leu Asp Glu Lys Ala Ala Ala Glu
     210                 215                 220

Lys Ala Ala Gln Glu Ala Ala Lys Lys Gln Ala Ala Tyr Glu Ala Gln
225                 230                 235                 240

Gln Lys Glu Ala Ala Gln Ala Gln Ala Ala Ser Thr Ala Ala Thr Ala
                 245                 250                 255

Lys Ala Val Glu Ala Ala Thr Ser Ser Ala Ser Ala Ser Ser Ser Gln
             260                 265                 270

Ala Pro Gln Val Ser Thr Ser Thr Asp Asn Thr Thr Ser Asn Ala Ser
         275                 280                 285

Ala Ser Asn Ser Ser Asn Ser Ser Asn Ser Ser Ser Ser Ser Ser Ser
     290                 295                 300

Ser Ser Ser Ser Ser Ser Ser Ser Ser Ser Asn Ser Asn Ala Gly Gly
305                 310                 315                 320

Asn Thr Asn Ser Gly Thr Ser Thr Gly Asn Thr Gly Gly Thr Thr Thr
                 325                 330                 335

Gly Gly Ser Gly Ile Asn Ser Ser Pro Ile Gly Asn Pro Tyr Ala Val
             340                 345                 350

Gly Gly Cys Thr Asp Tyr Val Trp Gln Tyr Phe Ala Ala Gln Gly Ile
         355                 360                 365

Tyr Ile Arg Asn Ile Met Pro Gly Asn Gly Gly Gln Trp Ala Ser Asn
     370                 375                 380

Gly Pro Ala Gln Gly Val Leu His Val Val Gly Ala Ala Pro Gly Val
385                 390                 395                 400

Ile Ala Ser Ser Phe Ser Ala Asp Phe Val Gly Tyr Ala Asn Ser Pro
                 405                 410                 415

Tyr Gly His Val Ala Ile Val Lys Ser Val Asn Ser Asp Gly Thr Ile
             420                 425                 430

Thr Ile Lys Glu Gly Gly Tyr Gly Thr Thr Trp Trp Gly His Glu Arg
         435                 440                 445

Thr Val Ser Ala Ser Gly Val Thr Phe Leu Met Pro Asn
450                 455                 460
```

( 2 ) INFORMATION FOR SEQ ID NO:3:

( i ) SEQUENCE CHARACTERISTICS:
        ( A ) LENGTH: 279 base pairs
        ( B ) TYPE: nucleic acid
        ( C ) STRANDEDNESS: double
        ( D ) TOPOLOGY: linear ( i i ) MOLECULE TYPE: DNA (recombinant)

( v i ) ORIGINAL SOURCE:
        ( C ) INDIVIDUAL ISOLATE: Hybrid gene: MSP signal (base pair 1
        to 81)/desulfatohirudin (base pair 82 to 279)

( v i i ) IMMEDIATE SOURCE:
        ( B ) CLONE: pUCRS/pML310

( i x ) FEATURE:
        ( A ) NAME/KEY: CDS
        ( B ) LOCATION: 1..276

( i x ) FEATURE:
        ( A ) NAME/KEY: mat_peptide
        ( B ) LOCATION: 82..276

( x i ) SEQUENCE DESCRIPTION: SEQ ID NO:3:

```
ATG  AAA  AAA  AAG  ATT  ATC  TCA  GCT  ATT  TTA  ATG  TCT  ACA  GTG  ATA  CTT        48
Met  Lys  Lys  Lys  Ile  Ile  Ser  Ala  Ile  Leu  Met  Ser  Thr  Val  Ile  Leu
-27       -25                      -20                      -15

TCT  GCT  GCA  GCC  CCG  TTG  TCA  GGT  GTT  TAC  GCT  GTT  GTT  TAC  ACC  GAC        96
Ser  Ala  Ala  Ala  Pro  Leu  Ser  Gly  Val  Tyr  Ala  Val  Val  Tyr  Thr  Asp
          -10                      -5                        1                 5

TGC  ACC  GAA  TCT  GGT  CAG  AAC  CTG  TGC  CTG  TGC  GAA  GGT  TCT  AAC  GTT       144
Cys  Thr  Glu  Ser  Gly  Gln  Asn  Leu  Cys  Leu  Cys  Glu  Gly  Ser  Asn  Val
                         10                      15                       20

TGC  GGT  CAG  GGT  AAC  AAA  TGC  ATC  CTG  GGT  TCT  GAC  GGT  GAA  AAA  AAC       192
Cys  Gly  Gln  Gly  Asn  Lys  Cys  Ile  Leu  Gly  Ser  Asp  Gly  Glu  Lys  Asn
               25                        30                       35

CAG  TGC  GTT  ACC  GGC  GAA  GGT  ACC  CCG  AAA  CCG  CAG  TCT  CAC  AAC  GAC       240
Gln  Cys  Val  Thr  Gly  Glu  Gly  Thr  Pro  Lys  Pro  Gln  Ser  His  Asn  Asp
          40                        45                        50

GGT  GAC  TTC  GAA  GAA  ATC  CCG  GAA  GAA  TAC  CTG  CAG  TAG                      279
Gly  Asp  Phe  Glu  Glu  Ile  Pro  Glu  Glu  Tyr  Leu  Gln
     55                        60                        65
```

( 2 ) INFORMATION FOR SEQ ID NO:4:

( i ) SEQUENCE CHARACTERISTICS:
        ( A ) LENGTH: 92 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Lys  Lys  Lys  Ile  Ile  Ser  Ala  Ile  Leu  Met  Ser  Thr  Val  Ile  Leu
-27       -25                      -20                      -15

Ser  Ala  Ala  Ala  Pro  Leu  Ser  Gly  Val  Tyr  Ala  Val  Val  Tyr  Thr  Asp
          -10                      -5                        1                 5

Cys  Thr  Glu  Ser  Gly  Gln  Asn  Leu  Cys  Leu  Cys  Glu  Gly  Ser  Asn  Val
                         10                      15                       20

Cys  Gly  Gln  Gly  Asn  Lys  Cys  Ile  Leu  Gly  Ser  Asp  Gly  Glu  Lys  Asn
               25                        30                       35

Gln  Cys  Val  Thr  Gly  Glu  Gly  Thr  Pro  Lys  Pro  Gln  Ser  His  Asn  Asp
          40                        45                        50
```

| Gly | Asp | Phe | Glu | Glu | Ile | Pro | Glu | Glu | Tyr | Leu | Gln |
|-----|-----|-----|-----|-----|-----|-----|-----|-----|-----|-----|-----|
|     |     |     | 55  |     |     |     | 60  |     |     |     | 65  |

BACTERIAL SHUTTLE VECTORS

This application is a continuation, of application Ser. No. 07/672,205 filed Mar. 19, 1991, now abandoned.

FIELD OF THE INVENTION

The invention relates to the field of genetic engeneering and provides novel DNA molecules which comprise multi-functional origins of replication and/or a DNA sequence coding for the most abundant protein in the supernatant of cultures of *Lactococcus lactis*, hereinafter named Major Secretion Product (MSP), for its signal peptide and/or the promoter of the MSP gene. The novel DNA molecules are used for the production of novel shuttle vectors for cloning of DNA in at least *E. coli* and Lactococcus spec. or novel vectors for the expression of homologous or heterologous genes and the production of secreted gene products in gram positive bacteria such as Lactococcus spec. and Bacillus spec.

BACKGROUND OF THE INVENTION

Although in genetic engineering techniques numerous procaryotic vector-host-systems for cloning of heterologous or homologous genes are already known, there is a continuous need for novel systems which may have advantages over the known systems.

Most recombinant work in DNA technology has been carried out with bacteria such as *Escherichia coli* or *Bacillus subtilis*. The lactic acid bacteria, however, are of much more industrial interest. For this reason, a number of efforts have been made to develop plasmid vectors for cloning and expression of homologous and heterologous genes in lactic acid bacteria, particularly in Lactobacillus spec. and Lactococeus spec. [see PCT WO 85/03945, Gasson and Anderson (1985), EP-A-0 316 677, Bates et al. (1989), Joset al. (1985) and review articles of Chassy (1987) and of De Vos (1987)]. Lactococcus spec. was formerly named Streptococcus spec.

Lactococcal strains investigated so far harbour a characteristic plasimid complement consisting of multiple different plasmids. This property can be used to differentiate between various lactococcal strains (Davies et al., 1981). For genetic studies, plasmid free strains have been constructed by repeated curing in the course of plasmid function studies (De Vos, 1987).

For example, the plasmid complement of *L. lactis* 712, hereinafter also called *L. lactis* LL712, consists of 5 plasmids having the molecular weights of 1.8 Md, 2.5 Md, 5.2 Md, 9 Md and 33 Md which are named pSH71, pSH72, pSH73, pSH74 and pLP712, respectively (Gasson, 1983).

Based on plasmid pSH71 of *L. lactis* and on the related *L. cremoris* plasmid pWV01 (Otto et al., 1982) various cloning vectors have been constructed. The cloning vectors have been produced either by inserting genetic markers such as antibiotic resistance genes into the plasmids or by screening fragments of the plasmids for an origin of replication function, i.e. for the ability to sustain replication of selected DNA fragments. A cloning vector produced according to the latter method is pNZ12 which contains the 1.7 kbp ClaI restriction fragment of pSH71 comprising the origin of replication (Gasson and Anderson, 1985). The origin of replication of pSH71 is also functional in other gram-positive bacteria such as Bacillus spec. and in the gram-negative *Escherichia coli*.

On the basis of these plasmids cloning vectors useful for the introduction and expression of homologous or heterologous genes in lactic acid bacteria have been developed. The development of the cloning vectors resulted in transformed lactococcal strains with improved properties which are useful in food and feed industry, for example a bacteriophage resistant *L. lactis* strain (EP-A-0 316 677) or a *L. tactis* strain which produces bovine prochymosin (PCT WO 85/03945). The development of cloning vectors for the production of homologous or heterologous gene products is not only of interest because of the production of improved lactic acid bacteria cells but also for the production of recombinant proteins. One of the major problems with the production of heterologous proteins in microbial expression systems has been the purification of the product. Purification of intracellular proteins is time-consuming and often results in poor yields. Purification can be considerably facilitated if the product is secreted from the host cell. To avoid the problems of purification of the products expressed in bacteria, vector-host systems for the production of recombinant proteins which are secreted into the supernatant can be useful.

Another advantage of secreted proteins can be that they can have a native and biologically active conformation, because then no refolding process is needed. Refolding is usually necessary if the polypeptide is intracellularly deposited.

Secretion of a protein usually requires a signal peptide at the amino terminus of the primary translation product which directs the protein into the secretory pathway. It is of advantage if the signal peptide is cleaved enzymatically from the protein during the translocation through the cell membrane. This, however, is not always the case.

OBJECT OF THE INVENTION AND SOLUTIONS

It is an object of the invention to provide novel hybrid vectors which can replicate in gram positive and gram negative bacteria and/or which allow expression of homologous or heterologous genes and secretion of stable protein products into the supernatant.

In particular, this object has been achieved by the present novel hybrid vectors comprising a novel DNA insert which comprises the promoter region, the DNA sequence coding for the signal peptide and the coding region of a hitherto unknown gene encoding a polypeptide which is the most abundant protein in the supernalant of *L. lactis* as judged after TCA precipitation of the supernalant, SDS-polyacrylamide electrophoresis of the precipitated proteins and staining of the gel with Coomassie brilliant blue and which is called herein Major Secretion Product (MSP).

A further solution to an object of the invention are novel hybrid vectors comprising an origin of replication derived from the 2.5 Md or 5.2 Md plasmid of *L. lactis* LL712, or an origin of replication related thereto, which is functional in gram positive as well as in gram negative bacteria.

Accordingly, another solution to an object of the invention is to provide novel hybrid vectors comprising the promoter region, the DNA sequence coding for the signal peptide and/or the coding region of the MSP gene or of a related gene and an origin of replication derived from the 2.5 Md or 5.2 Md plasmid of *L. lactis* LL712 or an origin of replication related thereto.

The invention concerns also functional fragments of the novel DNA inserts or the origins of replication per se. They are useful for the production of novel expression vectors for the secretion of homologous or heterologous proteins from lactic acid bacteria.

The invention further provides a method for the preparation of the novel DNA molecules and hybrid vectors, and a method for the production of secreted gene products by means of hosts transformed with a novel hybrid vector of the invention.

The invention provides also the MSP protein in pure form.

DETAILED DESCRIPTION OF THE INVENTION

DNA molecules

Figure 1:
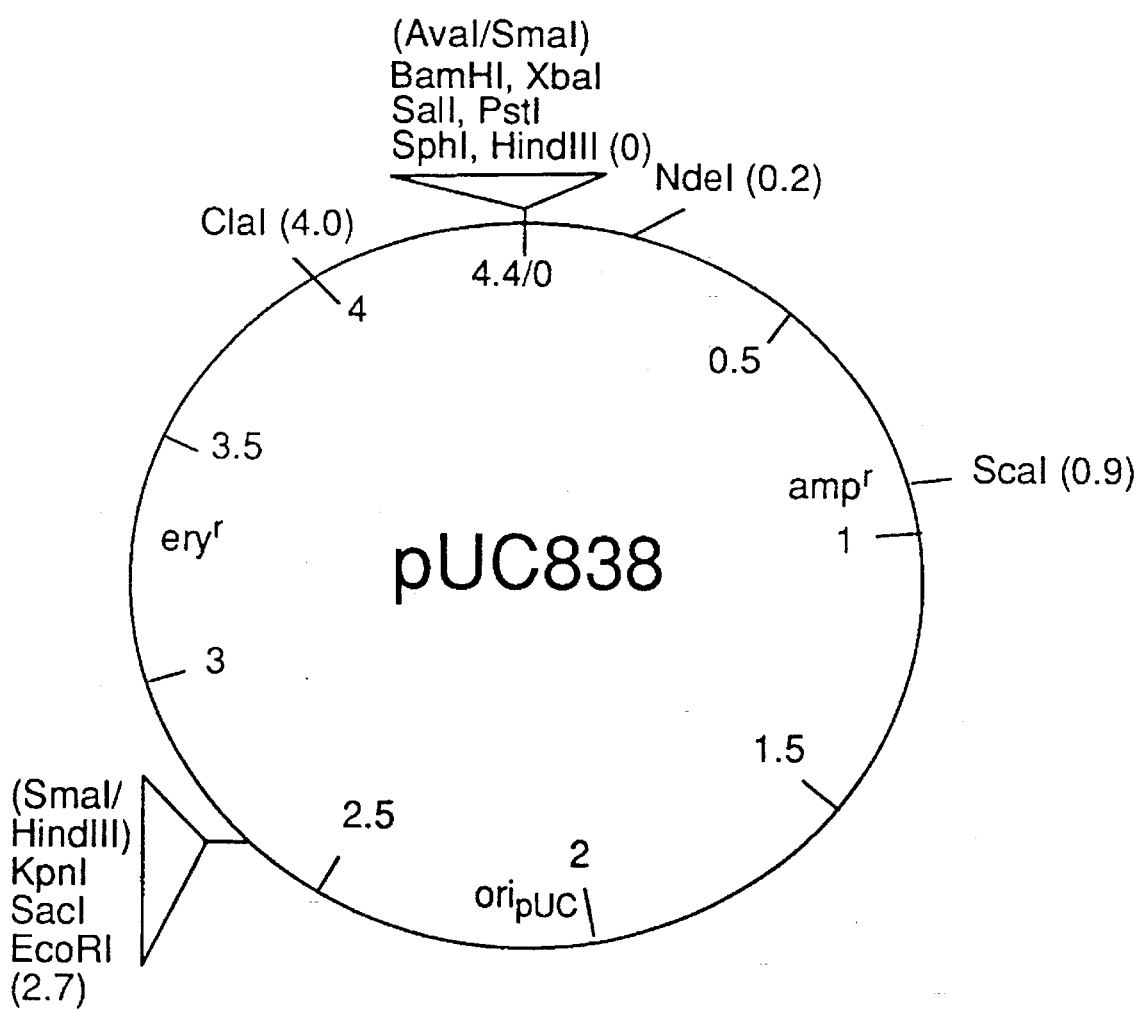

The invention concerns a hybrid vector comprising a) the approximately 3.5 kbp EcoRI/SalI *L. lactis* insert of the plasmid pUCRS, or a functional fragment thereof, or b) a DNA sequence which hybridizes with said insert or with a functional fragment thereof, or comprises a promoter region which is naturally operatively linked to such a hybridizing DNA sequence, or c) a degenerate sequence of a DNA sequence which is covered in a) or b) and which encodes a signal peptide, or d) a derivative of a DNA molecule covered in a), b) or c), and/or e) the origin of replication of (I) the 2.5 Md plasmid of *L. lactis* LL712, or of (II) the 5.2 Md plasmid of *L. lactis* LL712 or of (III) a plasmid of the same incompatibility group as the 2.5 Md plasmid or the 5.2 Md plasmid of *L. lactis* LL712.

The approximately 3.5 kbp EcoRI/SalI *L. lactis* insert of the plasmid pUCRS comprises the promoter region of the MSP gene, the DNA sequence encoding the MSP signal peptide and the coding region for MSP. MSP with its signal peptide attached is hereinafter named pre-MSP. The EcoRI/SalI insert comprises the 1920 bp long DNA sequence with the SEQ ID No. 1 depicted in the sequence listing in such orientation that base position 1 is proximal to the EcoRI site.

The coding region for MSP extends from base position 492 up to base position 1793 of the sequence with SEQ ID No. 1.

The DNA sequence which encodes the 27 amino acid long MSP signal peptide, extends from the end of the promoter region defined hereinafter up to the beginning of the DNA sequence coding for the mature MSP, i.e. from base position 411 up to position 491 of the sequence with SEQ ID No. 1. The MSP signal peptide or a functional fragment thereof causes a protein to be excreted from a host cell, e.g. from a lactic acid bacterium, such as *Lactococcus lactis*, or from Bacillus spec., such as *B. thuringiensis*, if the N-terminus of the protein is covalently linked to the C-terminus of the signal peptide. Covalent linkage of the C-terminus of the MSP signal peptide and the N-terminus of a protein which is to be excreted from a host cell can be obtained by the production of a fusion gene in which the entire DNA sequence encoding the MSP signal peptide or part thereof encoding a functional fragment of the MSP signal peptide comprising the C-terminus is linked in proper reading frame to the 5' end of a structural gene encoding the desired protein. Such a fusion gene is, for example, the DNA molecule with SEQ No. 2 which comprises the DNA sequence encoding the MSP signal peptide and the hirudin structural gene.

The amino acid sequences of the MSP signal peptide and of MSP are also given in the sequence with SEQ ID No. 1.

The promoter region of the MSP gene is located upstream of the DNA sequence encoding the MSP signal peptide and comprises up to about 1500, preferably up to about 100 to 1000 nucleotides. In the approximately 3.5 kbp long EcoRI/SalI *L. lactis* insert of the plasmid pUCRS, the promoter region extends from the EcoRI cut end of the insert located upstream of the base corresponding to position 1 of the DNA sequence with SEQ ID No. 1 up to base position 411. More particular, the promoter region extends from the first HindIII restriction site located upstream of the base corresponding to position 1 up to base position 411. The promoter region can bind RNA polymerase as well as regulatory proteins and can control the expression of a structural gene operatively linked therewith.

The term functional fragment includes those DNA fragments retaining promoter, signal and/or structural functions.

Preferred functional fragments are those containing the MSP promoter region, the DNA sequence encoding the MSP signal peptide or the promoter region and the DNA sequence encoding the MSP signal peptide. Fragments according to the invention are also composed of smaller fragments retaining the MSP promoter activity and/or coding for a peptide with signal peptide activity.

Fragments with promoter function, for example, are those starting with the first base at the EcoRI cut end of the approximately 3.5 kbp EcoRI/SalI *L. lactis* insert or, in particular, those starting at the HindIII site and extending up to a base corresponding to about position 410 of the sequence with SEQ ID No. 1. Other fragments with promoter function are selected from the group of fragments starting with any one of the bases between the EcoRI and the HindIII site and ending with a base in about position 410 of the sequence with SEQ ID No. 1. Shorter fragments of the promoter region also retain promoter activity.

A DNA fragment which encodes a signal peptide extends, for example, from about base 411 up to base 491 of the sequence with SEQ ID No. 1. It can be extended at the 5' end with a fragment of the promoter region which does not retain promoter activity.

A fragment retaining MSP promoter function and encoding a signal peptide extends from the EcoRI cut end of the insert located upstream of the base corresponding to position 1 of the DNA sequence with SEQ ID No. No. 1 down to base position 491. Another fragment retaining MSP promoter function and encoding a signal peptide extends from the first HindIII restriction site located upstream of the base corresponding to position 1 of DNA sequence with SEQ ID No. 1 up to about the base corresponding to position 491. Other fragments retaining MSP promoter function and encoding a signal peptide are selected from the group of fragments starting with anyone of the bases between the said EcoRI and HindIII sites and ending with a base in about position 491 of the sequence with SEQ ID No. 1.

The fragments may contain linkers which provide for succesful linkage to other DNA molecules. Suitable linkers to above fragments have a DNA sequence which fits into the restriction site of the DNA to which the fragment is to be linked. They may also contain a predetermined restriction site.

A DNA molecule which hybridizes with said insert is hybridizing under conventional conditions. A conventional hybridization procedure is described e.g. by Benton and Davis (1977). Such a hybridizing DNA molecule comprises, for example, as hybridizing DNA sequence a variant of the structural gene encoding MSP. Such a hybridizing variant is hereinafter also referred to as a structural gene related to the MSP gene. The protein encoded by such a related gene is referred to as a protein related to MSP. Accordingly, a promoter region which is naturally operatively linked to a DNA sequence hybridizing with said insert is a promoter region of a gene related to the MSP gene.

A structural gene related to the MSP gene is, for example, a naturally occurring variant derived from another bacterium than *L. lactis*, particularly from another lactic acid bacterium, for example from Lactobacillus spec, or Lactococcus spec, e.g. *L. cremoris* or *L. thermophilus*. It is also a naturally occuring variant which is encoded by an isogene on the chromosome of or on a plasmid naturally occuring in *L. lactis*.

A DNA molecule comprising a gene related to the MSP gene can be isolated according to conventional methods.

DNA molecules of the invention are also such having degenerated DNA sequences. They are degenerated within the meaning of the genetic code in that an unlimited number of nucleotides are replaced by other nucleotides without changing the amino acid sequence for which they code. Molecules having such degenerate DNA sequences may be useful because of their different restriction sites or because of a preferred codon usage in a particular host. Preferred are degenerated sequences of the DNA sequence coding for the MSP signal peptide or of a variant thereof.

The term derivative when used in connection with a DNA molecule covered in a), b) or c) includes fragments, mutants or larger derivatives of such a DNA molecule. The term derivative includes also larger derivatives of fragments or mutants of such a DNA molecule. Preferred are fragments retaining promoter, signal or structural functions. Examples of such fragments are given above.

A mutant of a DNA molecule described in a), b) or c) is, for example, a DNA molecule having a deletion, insertion, inversion, or point mutation which may occur naturally or may be artificially introduced into the DNA molecule in vivo or in vitro according to conventional methods. A mutant can show an altered restriction pattern.

Larger derivatives of a DNA molecule covered in a), b) or c) are, for example, excisable from the *L. lactis* genome. They can be found in a genomic library of *L. lactis* LM0230 obtained by fragmentation of the nucleic acids, treatment of the fragments with a suitable restriction enzyme, e.g. Sau3AI, EcoRI, BamHI or HindIII, ligating into a suitable vector, e.g. the lambda phage λEMBL3 or the plasmid pBR322, cloning, e.g. in *E. coli*, and excising again, with the same or another suitable restriction enzyme.

Larger derivatives of a DNA molecule covered in a), b) or c) are also recombinant DNA molecules with flanking sequences, for example such comprising linkers which provide suitable restriction sites or which put regulatory sequences, such as a promoter, a DNA sequence encoding a signal peptide or a terminator, and a structural gene into the correct distance or reading frame, or such comprising sequences derived from a vector, e.g. from a phage or plasmid used in the construction of a hybrid vector. The flanking sequences comprised in the larger derivatives may give rise to fusion genes.

An origin of replication derived from the *L. lactis* LL712 2.5 Md or 5.2 Md plasmid or from a plasmid of the same incompatibility group as the 2.5 Md plasmid or the 5.2 Md plasmid can cause a plasmid to replicate in acid bacteria, for example in lactococci, e.g. in *L. lactis*, *L. lactis diacetylactis* or *L. cremoris*, and in *E. coli* or also in gram negative bacteria other than *E. coli* or in gram positive bacteria other than lactic acid bacteria, e.g. in Bacillus spec. such as *B. thuringiensis*.

An origin of replication which is derived from the *L. lactis* LL712 2.5 Md or 5.2 Md plasmid or from a plasmid of the same incompatibility group as the 2.5 Md plasmid or the 5.2 Md plasmid is, for example, comprised in the whole respective linearized plasmid obtainable after treatment with a suitable restriction endonuclease. Accordingly, a hybrid vector of the invention is also such comprising the whole DNA sequence of the 2.5 Md or the 5.2 Md plasmid or of a plasmid of the same incompatibility group as the 2.5 Md or 5.2 Md plasmid. Both plasmids can be isolated, for example, from the strain *L. lactis* LL712 which is deposited with the DSM as DSM 5804.

A DNA sequence which functions as an origin of replication is also a fragment of any of said plasmids retaining origin of replication function. Such a DNA fragment can be obtained, for example, by isolating it after the fragmentation of the respective plasmid or of a fragment thereof, for example, with physical forces, e.g. sharing forces, or with chemical cleavage reactions, or with enzymes cleaving DNA such as nucleases, e.g. the exonucleases Bal31, S1 or exonuclease III, or endonucleases, e.g. restriction endonucleases. In particular, such a DNA fragment is a restriction fragment obtained after treatment of the respective plasmid or fragment therof with one or with two different restriction endonucleases which are in the case of the 2.5 Md plasmid, for example, NdeI, SphI and/or EcoRV and in the case of the 5.2 Md plasmid, for example, Sau3A, NdeI, HindIII, AccI and/or EcoRI.

Figure 2:
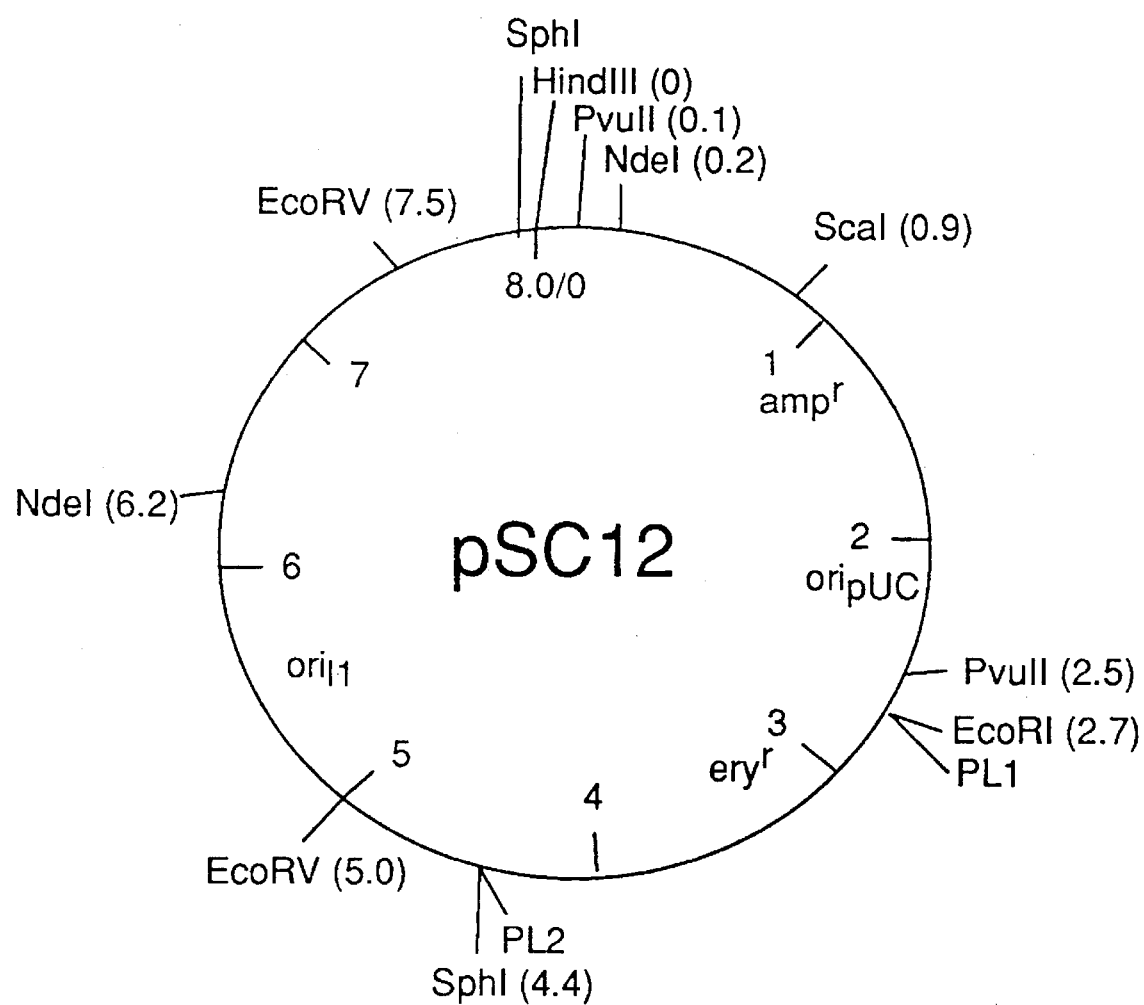

The origin of replication of the 2.5 Md plasmid is located, for example, on the approximately 1.8 kbp long NdeI/SphI fragment, the approximately 3.1 kbp long EcoRV/SphI fragment obtainable after partial EcoRV digestion of the approximately 3.5 kbp long SphI fragment, the approximately 3.5 kbp long SphI fragment, the approximately 1.2 kbp long NdeI/EcoRV fragment, the approximately 2.5 kbp long EcoRV fragment, or the approximately 3.5 kbp long EcoRV/SphI fragment obtainable after partial EcoRV digestion of the approximately 3.5 kbp long SphI fragment. The approximately 3.5 kbp long SphI and the other fragments mentioned hereinbefore are also comprised in pSC12. The production of pSC12 is described in Example 1.2. A restriction map is given in FIG. 2.

Figure 3:
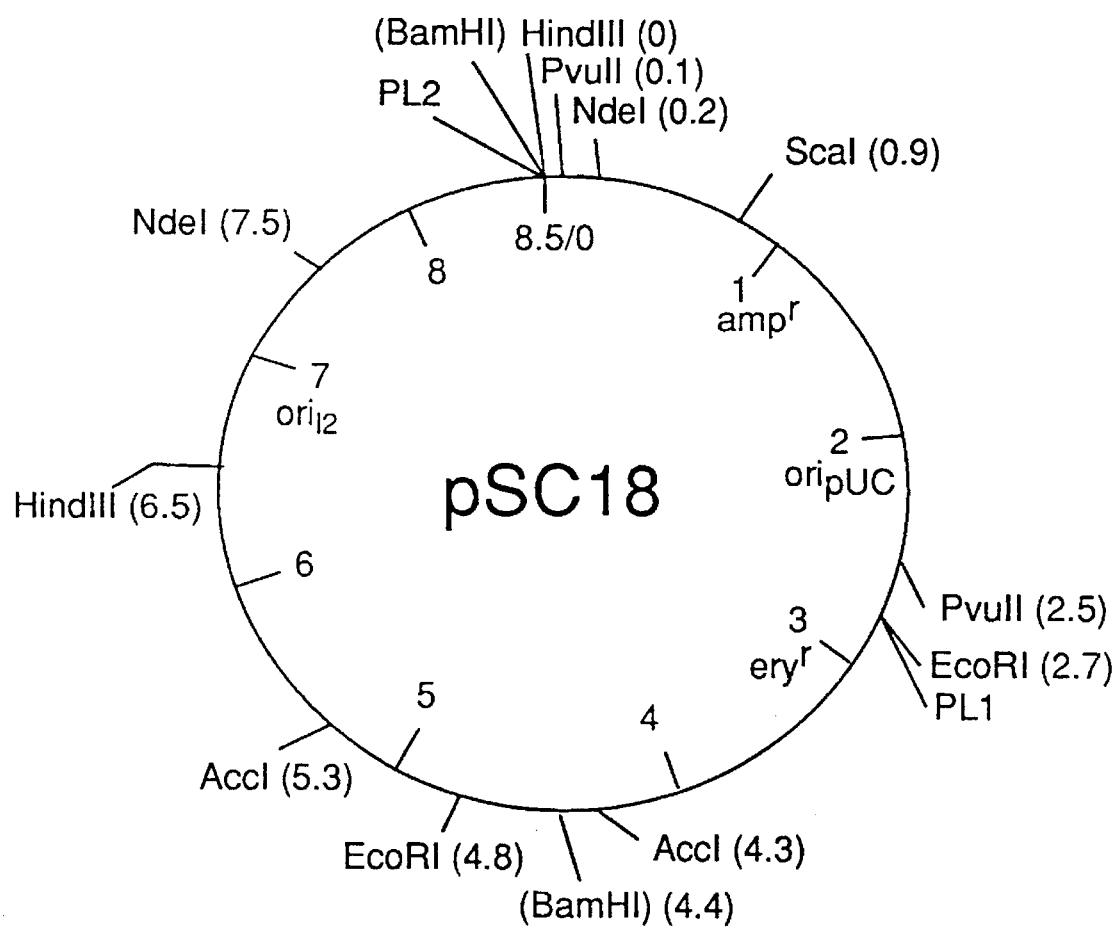

The origin of replication of the 5.2 Md plasmid is located, for example, on the approximately 1.0 kbp long NdeI/HindIII fragment, the approximately 2.2 kbp long NdeI/AccI fragment, the approximately 2.7 kbp long NdeI/EcoRI fragment, the approximately 3.1 kbp long NdeI/Sau3A fragment, the approximately 2.0 kbp long Sau3A/HindIII fragment, the approximately 3.2 kbp long Sau3A/AccI fragment, the approximately 3.7 kbp long Sau3A/EcoRI fragment, or the approximately 4.1 kbp long Sau3A fragment. The fragments with Sau3A cut ends are obtainable after partial Sau3A digestion of the 5.2 Md plasmid, of pSC18 or of suitable restriction fragments of these plasmids. The production of pSC 18 is described in Example 1.3. A restriction map is given in FIG. 3.

Plasmids of the same incompatibility group cannot stably coexist in the same cell. They carry related origins of replication.

A recombinant DNA molecule does, for example, contain linkers and/or sequences derived from a vector such as from a phage or plasmid, and optionally a marker gene such as a resistance marker gene, e.g. an erythromycin, ampicillin, or tetracyclin resistance marker gene or the like. A recombinant DNA molecule comprising an origin of replication of the present invention is, for example, a vector plasmid for lactic acid bacteria, preferentially a shuttle vector which can replicate at least in lactic acid bacteria and *E. coli* and wherein a lactococcal derived origin of the invention is the only origin of replication.

A preferred shuttle vector is pSC12, pSC12ΔP, pSC12ΔN, pSC12ΔNP, pSC18, pSC18ΔP, or pSC18ΔN. A preferred shuttle vector for the expression of a foreign gene in lactic acid bacteria is pSC12HIR, pSC12HIR-1 or pSC12HIRTerm. The preferred shuttle vectors are described in the Examples.

A DNA sequence which functions as an origin of replication in at least lactic acid bacteria and *E. coli* which is intended to be covered above under e) is also an inversion, insertion, deletion or point mutant of a DNA sequence defined hereinbefore which retains the function of an origin of replication. Such mutants have an altered nucleotide sequence in the DNA sequences flanking the real origin of replication, for example point mutations which cause an altered pattern of restriction sites or deletion mutants such as the *L. lactis* inserts of the plasmids pSC12ΔP, pSC12ΔN, pSC12ΔNP, pSC18ΔP, or pSC18ΔN (see Table 1). The real origin of replication mentioned hereinbefore is intended to be the smallest DNA fragment which functions as an origin of replication.

The hybrid vectors of the invention are usable for cloning in hosts such as fungi or in particular bacteria. They can be derived from any vector useful in the art of genetic engineering, such as from phages, cosmids or plasmids. They are, for example, derivatives of phage λ, e.g. NM 989 or EMBL 3, of phage M13, e.g. M13mp18 or M13mp19, of bacterial plasmids, e.g. pBR 322, pUC18 or pUC19 or plasmids of lactic acid bacteria, or of yeast plasmids, e.g. yeast 2μ plasmid, or also of defective phages or defective plasmids in the presence of a helper phage or a helper plasmid allowing replication of said defective phages or plasmids.

A hybrid vector of the invention comprises a nucleotide sequence of a DNA molecule covered in a), b), c) or d). It comprises in particular the approximately 3.5 kbp EcoRI/ SalI *L. lactis* insert, a fragment thereof coding for the MSP signal peptide and/or the promoter of the MSP gene. Depending on the type of the DNA molecule of the invention inserted in the hybrid vector, the vector may comprise a hybrid expression control sequence. Such a hybrid expression control sequence partially consists of a DNA molecule covered in a), b) or c) and partially of a DNA molecule different from a DNA molecule covered in a), b) or c). For example, the hybrid vector can comprise the MSP promoter in combination with a DNA sequence coding for a non-MSP signal peptide a DNA fragment coding for the MSP signal peptide in combination with another than the MSP promoter. Additionally, a hybrid vector of the invention optionally comprises a transcriptional terminator region, e.g. the trpA transcription terminator of *E. coli*.

Hybrid vectors comprising a DNA sequence coding for a signal peptide of the present invention, i.e. derived from the gene for pre-MSP or a related gene, are useful for the production of secreted gene products in lactic acid bacteria, particularly in Lactococcus spec., especially in *L. lactis* or *L. cremoris* or in other bacteria, for example a Bacillus spec. such as *B. thuringiensis*. Such a hybrid vector comprises a promoter which functions in the desired bacterium, for example the MSP promoter for the expression in lactic acid bacteria, and optionally a transcription terminator region which functions in the desired bacterium. The use of a terminator can increase the yield of the recombinant gene product if it is operatively linked with the respective homologous or heterologous structural gene. For example, if the trpA terminator of *E. coli* is operatively linked with a hirudin gene which is expressed under the control of the MSP promoter and a DNA molecule encoding the MSP signal peptide in lactic acid bacteria, the production of desulfatohirudin is markedly increased.

A hybrid vector of the invention also comprises an origin of replication which functions in the desired host, e.g. in lactic acid bacteria and/or Bacillus spec. and/or *E. coli*.

A DNA sequence bearing an origin of replication which functions in at least lactic acid bacteria is, for example, the 1.7 kbp ClaI fragment of the lactococcal plasmid pSH71 (Gasson and Anderson, 1985) or one of the DNA fragments defined hereinbefore which comprise the origin of replication of the 2.5 Md plasmid or of the 5.2 Md plasmid of *L. lactis* LL712.

A hybrid vector of the present invention may contain a selectable marker. The choice of the marker depends on the host which is to be transformed, selected and cloned. Any marker gene can be used which facilitates the selection of transformants due to the phenotypic expression of the marker. Suitable markers are particularly those expressing antibiotic resistance, e.g. against erythromycin, tetracycline or ampicillin, or in the case of auxotrophic mutants, genes which complement host lesions, e.g. genes of the lactose metabolizing pathway.

Preferred embodiments of the present invention are hybrid vectors comprising a homologous or heterologous structural gene, for example the MSP or especially a heterologous structural gene defined hereinafter, which is operatively linked in a proper reading frame to the DNA sequence encoding the MSP signal peptide and which can be expressed under the control of the MSP promoter or a heterologous promoter.

Structural genes may originate from viruses, procaryotic cells or eucaryotic cells and may be derived from genomic DNA or from cDNA prepared via the mRNA route, or may be synthesized chemically. They may code for a wide variety of useful polypeptides, including glycosylated polypeptides, in particular of higher eukaryotic, especially mammalian, such as animal or especially human origin, such as enzymes which can be used, for example, for the production of nutrients and for performing enzymatic reactions in chemistry, or polypeptides which are useful and valuable for the treatment of human or animal diseases or for the prevention thereof, for example hormones, polypeptides with immunomodulatory, anti-viral and anti-tumor properties, antibodies, viral antigens, vaccines, clotting factors, foodstuffs, and the like.

Examples of such heterologous structural genes are e.g. those coding for hormones such as secretin, thymosin, relaxin, calcitonin, luteinizing hogone, parathyroid hormone, adrenocorticotropin, melanocyte-stimulating hormone, β-lipotropin, urogastrone or insulin, growth factors, such as epidermal growth factor, insulin-like growth factor (IGF), e.g. IGF-I and IGF-II, mast cell growth factor, nerve growth factor, glia derived nerve cell growth factor, or transforming growth factor (TGF), such as TGFβ, growth hormones, such as human or bovine growth hormones, interleukin, such as interleukin-1 or -2, human macrophage migration inhibitory factor (MIF), interferons, such as human α-interferon, for example interferon-αA, αB, αD or αF, β-interferon, γ-interferon or a hybrid interferon, for example an αA-αD- or an αB-αD-hybrid interferon, especially the hybrid interferon BDBB, proteinase inhibitors such as $α_1$-antitrypsin, SLPI and the like, hepatitis virus antigens, such as hepatitis B virus surface or core antigen or hepatitis A virus antigen, or hepatitis nonA-nonB antigen, plasminogen activators, such as tissue plasminogen activator or urokinase, tumour necrosis factor, somatostatin, renin, β-endorphin, immunoglobulins, such as the light and/or heavy chains of immunoglobulin D, E or G, or human-mouse hybrid immunoglobulins, immunoglobulin binding factors, such as immunoglobulin E binding factor, e.g. sCD23, calcitonin, human calcitonin-related peptide, blood clotting factors, such as factor IX or VIIIc, erythropoietin, eglin, such as eglin C, hirudin, desulfatohirudin, such as desulfatohirudin variant HV1, HV2, HV3, [Leu$^1$, Thr$^2$]-HV1, [Lys$^{47}$]-HV2 or PA, human superoxide dismutase, viral thymidin kinase, β-lactamase, glucose isomerase. A preferred gene is this coding for desulfatohirudin, e.g. variant HV1. In the hybrid vectors of the present invention, the present promoter and/or the DNA molecule encoding the MSP signal peptide is operably linked to the polypeptide coding region so as to ensure effective expression of the polypeptide.

Preferred hybrid vectors are pUCRS, M13 mp18RS, M13 mp19H, pVAHIR, pVAHIR-1, pSC12HIR, pSC12HIR-1, and in particular pSC12HIRTerm. The hybrid vectors are described hereinafter in the Examples.

The invention also concerns a DNA molecule which a) is the approximately 3.5 kbp EcoRI/SalI *L. lactis* insert of the plasmid pUCRS, or a functional fragment thereof, or b) hybridizes with said insert or with a functional fragment thereof, or comprises a promoter region which is naturally operatively linked to such a hybridizing DNA sequence, or c) is a degenerate sequence of a DNA sequence which is covered in a) or b) and which encodes a signal peptide, or d) is a derivative of a DNA molecule covered in a), b) or c), and/or e) comprises the origin of replication of (I) the 2.5 Md plasmid of *L. lactis*LL712, or of (II) the 5.2 Md plasmid of *L. lactis* LL712, or of (III) a plasmid of the same incompatibility group as the 2.5 Md plasmid or the 5.2 Md plasmid of *L. lactis* LL712 per se. These DNA molecules are useful for the preparation of the hybrid vectors of the invention or for screening DNA gene libraries or mRNA for further similar DNAs or mRNAs.

Process for the Preparation of the DNA Molecules and of MSP

A further object of the invention is a process for the preparation of a DNA molecule of the invention, i.e. of a hybrid vector or a DNA molecule defined hereinbefore, comprising A) culturing a host which comprises a DNA molecule of the invention and isolating a DNA molecule of the invention from such a cultured host, or B) preparing a DNA molecule of the invention by an in vitro synthesis.

The culturing of the hosts is carried out in a conventional nutrient medium which may be supplemented with or deprived of chemical compounds allowing negative or positive selection of the transformants, i.e. such hosts containing the desired DNA molecule together with a selection marker, from the non-transformants, i.e. such hosts lacking the desired DNA molecule.

Any suitable transformable hosts useful in the art may be used, for example suitable bacteria, such as gram-negative bacteria, e.g. *E. coli*, or gram-positive bacteria, e.g. Bacillus spec. or lactic acid bacteria, such as Lactobacillus spec., or especially Lactococcus spec., e.g. *L. lactis, L. lactis* diacetylactis or *L. cremoris*.

Bacteria are transformed by a conventional method and the transformants are identified in conventional manner, e.g. by their resistance, for example against tetracycline.

In particular the described hybrid vectors are propagated in suitable *E. coli* host strains, such as TG1, HB 101, JM109, MH1 and the like, or in suitable Bacillus strains, or in suitable lactic acid bacteria, e.g. Lactococcus strains such as *L. lactis* 0230, *L. lactis diacetylactis, L. cremoris* and the like. The hosts are transformed and selected by methods conventional in the art. The propagated plasmid DNA is isolated from the bacteria by conventional methods, for example as described by Birnboim & Doly (1979).

A DNA molecule of the invention can also be prepared by an in vitro synthesis according to conventional methods. The in vitro synthesis is especially applicable for the preparation of smaller fragments, e.g. of the DNA sequences of the MSP gene or of a related gene coding for the promoter or in particular for the signal peptide.

A DNA molecule of the invention can be obtained from a lactic acid bacterium containing such a DNA molecule, in particular from a genomic library thereof or also via mRNA.

In the following the preparation of a DNA molecule which is the approximately 3.5 kbp EcoRI/SalI *L. lactis* insert of plasmid pUCRS is described in more detail.

As starting material a genomic library of Lactococcus spec., e.g. *L. lactis* 0230, can be used which is prepared according to conventional methods, e.g. by partial digestion of genomic DNA of a *L. lactis* strain, e.g. LM 0230, C2 or LL712, with a restriction enzyme, e.g. Sau3A or MboI, and cloning the high molecular weight DNA fragments in a suitable vector, e.g. the *E. coli* plasmid pUN121 or a lambda phage, e.g. λEMBL3.

Any other strain of lactic acid bacteria producing MSP may also serve as source for the genomic library and likewise other suitable vectors may be used as recipient for the fragments.

In order to successfully screen the genomic library for DNA sequences of the present invention a DNA probe is necessary which hybridizes with such a DNA sequence, e.g. with the MSP structural gene. This can be a synthetic DNA probe if the sequence of e.g. the MSP gene or part thereof is known. As neither the MSP protein nor the MSP gene sequence or part thereof was known prior to the invention, the problems of purification of MSP, of the determination of the N-terminus sequence of MSP and of the preparation of hybridizing DNA probes were solved first.

MSP is the most abundant gene product in the supernatant of cultures of Lactococcus spec., e.g *L. lactis* as judged after TCA precipitation of the supernatant, SDS-polyacrylamide gel electrophoresis of the precipitated proteins and staining of the gel with Coomassie brilliant blue.

For the purification of MSP any source containing it may be used, for example, the supernatant of a culture of lactic acid bacteria, e.g. Lactococcus spec such as *L. lactis* . MSP can be purified from a SDS polyacrylamide gel by cutting out the gel piece comprising the major protein band and by eluting MSP.

Further purification methods such as precipitation with acid, e.g. trichloroacetic acid, salting out, desailing, reprecipitation in form of a different salt, dialysis chromatography, e.g. affinity chromatography, ion exchange chromatography, gel permeation chromatography, electrophoresis, e.g. with SDS-polyacrylamide gel, isoelectric focusing, electroelution, and the like, or any combination thereof can also be applied in order to obtain pure MSP.

In the present invention, a MSP with an apparent molecular weight of about 56 kD was isolated in pure form by precipitating the proteins from the supernatant of *L. lactis* LM0230 with trichloroacetic acid, by a subsequent electrophoresis of the precipitated protein on a SDS polyacrylamide gel, cutting out the region with the major protein band and electroeluting MSP from the gel. This method is also suitable for the isolation of proteins related to MSP having another apparent molecular weight. The amino acid sequence of MSP was partly determined by sequencing and partly deduced from the DNA sequence. It is shown in the sequence listing under SEQ ID No. 1 and extends from position 28 up to 466 of the amino acid sequence depicted.

The pure MSP protein is also a subject of the invention.

The sequencing of the N-terminus of MSP was performed in conventional manner and revealed the following amino acid sequence:

X-X-Asn-Ser-Asp-Ile-Ala-Lys-Gln-Asp-Ala-Thr-Ile-Ser-X-Ala-Gln-Ser-Ala-Lys-Ala- Gln-Ala-Gln-Ala-Gln-Val-Asp. The first two amino acids and the amino acid in position 15 which are indicated with "X" have not been determined.

Based on the sequence of the amino acids in position 5 to 13 the following oligonucleotide mixture was synthesized:

GAN$_1$ ATN$_2$ GCI AAN$_3$ CAN$_3$ GAN$_1$ GCI AC. In this nucleotide sequence, N$_1$ is T or C; N$_2$ is T, C or A; N$_3$ is A or G. A represents a nucleotide with the base Adenine, T with Thymine, C with Cytidine, G with Guanosine and I with Inosine. The oligonucleotide mixture was radioactively marked in conventional manner and used to screen a genomic library of Lactococcus spec., particularly *L. lactis* LM0230.

DNA probes containing sequences encoding MSP amino acid sequences and having at least about 14 bp can be used for screening for nucleic acids comprising related MSP genes or part thereof, which includes also the screening for mRNA coding for pre-MSP.

For screening purposes the DNA probes are radioactively labelled at their 5' end by methods known in the art using $\gamma^{32}$P-ATP and T4 kinase. Host microorganisms or phages carrying nucleic acids of the present invention as an insert, are identified by hybridization with the labelled DNA probe on filter replicas of the gene library.

The hybridization conditions used are conventional and may be more or less stringent, e.g. simply by choosing different temperatures.

The hybridizing part of a DNA clone of the library which hybridizes with the oligonucleotide mixture was partly sequenced according to conventional methods. The determined sequence comprises nearly the entire functional MSP gene. The sequence is depicted in the sequence listing under SEQ ID No. 1.

The 3.5 kbp EcoRI/SalI *L. lactis* insert can be isolated from positive clones of a genomic library by digestion with EcoRI and SalI and subsequent purification of the insert according to conventional methods, e.g. using agarose gel electrophoresis. Fragments can be prepared according to conventional methods and can be ligated into a suitable vector, e.g. into M13mp18 to generate M13mp18RS or into pUC18 to generate pUCRS.

Likewise, any other *L. lactis* insert comprising MSP sequences, for example larger derivatives, variants or fragments of the 3.5 kbp EcoRI/SalI insert, or DNA molecules which hybridize with the 3.5 kbp EcoRI/SalI insert or comprise a promoter region which is naturally linked to such a hybridizing DNA molecule can be isolated from a genomic library of lactic acid bacteria.

Fragments of the DNA molecule according to a) to c) may be obtained in conventional manner, e.g. by isolation of the fragments after digestion of the insert with suitable exo- or endonucleases, e.g. with exonuclease III, Bal31 or S1 or restriction endonucleases, such as Sau3A, HindIII, and the like. Fragments may also be obtained by in vitro DNA synthesis according to conventional methods.

Mutants of the DNA molecule covered in either of a) to c) hereinbefore, for example inversion, deletion, insertion or point mutants, can be prepared according to conventional methods, for example in vivo or in vitro by site-directed mutagenesis (see review article of Zoller and Smith 1983, Botstein and Shortle, 1985, or Norris et al., 1983) using mutagenic oligonucleotide primers or by deleting DNA fragments between two restriction sites by cutting with suitable restriction enzymes and religating the DNA, optionally in diluted solution.

In the following the preparation of a recombinant DNA molecule according to the invention comprising a DNA sequence which functions as an origin of replication is described in more detail.

Plasmids are isolated from *L. lactis* LL712 according to conventional methods, e.g. as described by Birnboim and Doly (1979) with the modifications described in the examples, and are separated in conventional manner, e.g. using chromatography techniques, for example agarose gel chromatography as described in Maniatis et al. (1982). The 2.5 Md plasmid and the 5.2 Md plasmid are isolated and fragmented according to conventional methods.

The fragment mixtures thus obtained are ligated with a suitable vector according to conventional methods, e.g. as described in Maniatis et al. (1982) and these ligation mixtures are used to transform in conventional manner a suitable intermediate host strain.

A suitable vector carries a marker gene for selection in lactic acid bacteria, e.g. a resistance marker gene, for example the erythromycin resistance gene, and an origin of replication which does not function in lactic acid bacteria but in a bacterium suitable as an intermediate host for cloning the fragments of the *L. lactis* plasmids. A suitable vector comprises also a marker gene for selection in the intermediate host which may be identical with the marker gene which functions in the lactic acid bacterium. A suitable intermediate host is, for example, an *E. coli* strain, e.g. *E. coli* TG1, and a suitable cloning vector then is an *E. coli* vector, for example a pUC18 derivative carrying an erythromycin resistance gene, such as pUC383, the construction of which is described hereinafter in the Examples.

The intermediate host cells which are transformed with a vector comprising fragments of the *L. lactis* 2.5 Md or 5.2 Md plasmid optionally may be selected in conventional manner which depends on the type of intermediate host cell and the vector used. Selection markers may be, for example, resistance markers or genes encoding a screenable marker enzyme, e.g. the product of the *E. coli* lacZ gene, β-galactosidase, provided that the host is an *E. coli* strain defective in the genomic lacZ gene. The selection marker genes may be disturbed by the insertion of a DNA fragment. If the marker is lacZ, the host cells which carry a vector with a fragment inserted into the lacZ gene are no more able to convert X-Gal into a blue dye and, as a consequence, positive clones on X-Gal comprising agar plates remain white after induction of the expression of the lacZ gene with IPTG.

Vectors carrying an insert derived from the *L. lactis* 2.5 Md or 5.2 Md plasmid are tested for their ability to replicate in a plasmid free *L. lactis* strain, e.g. in *L. lactis* 0230. For this purpose the plasmids are isolated from the intermediate host and transformed into *L. lactis* 0230 cells according to conventional methods, e.g. as described in Powell et al. (1988). Replicating vectors comprise a DNA insert derived from the *L. lactis* 5.2 Md or 2.5 Md plasmid which functions as an origin of replication. A DNA molecule comprising this function may be isolated from the replicting vectors, fragmentated, mutated and the like and can be used to construct recombinant DNA molecules according to the invention, e.g. cloning or expression vectors replicating in lactic acid bacteria. The *L. lactis* 2.5 Md or 5.2 Md plasmid derived origins of replication are also functional in bacteria other than lactic acid bacteria, e.g. in Bacillus spec. or *E. coli*. Therefore, vectors comprising such DNA fragments can be used as shuttle vectors.

Fragments of the 2.5 Md or 5.2 Md plasmid carrying an origin of replication can also be identified and isolated according to the method described hereinbefore from a fragment mixture which was obtained by fragmentation of the whole plasmid pool of *L. lactis* LL712. Which of the cloned fragments carrying an origin of replication is derived from the 2.5 Md or 5.2 Md plasmid may be determined by hybridizing the cloned fragments with the plasmids of the plasmid pool derived from *L. lactis* LL712 which were separated on an agarose gel or by comparison of the restriction pattern of the cloned fragments and of the plasmids of the pool.

Recombinant DNA molecules according to the invention which comprise the whole DNA sequence of the *L. lactis* 2.5 Md or 5.2 Md plasmid or a plasmid of the same imcompatibility group as the 2.5 Md or 5.2 Md plasmid may be obtained, for example, by cutting the respective plasmid with a suitable restriction endonuclease and ligating it, for example, with a DNA fragment comprising a homologous or heterologous structural gene, a promoter region or vector sequences or with a linker fragment or the like. Suitable restriction endonucleases have only one recognition and cleavage site in the respective plasmid.

A recombinant DNA molecule comprising a sequence with origin of replication function derived from the 2.5 Md or the 5.2 Md plasmid can be obtained, for example, by a method comprising the preparation of the plasmid pool of *L. lactis* LL712 according to conventional methods, the identification of the 2.5 Md or 5.2 Md plasmid, e.g. by estimating the molecular weight in agarose gel electrophoresis, fragmentation of the respective plasmid, e.g. with suitable restriction enzymes, preparation of a fragment comprising the origin of replication function, e.g. one of the fragments mentioned hereinbefore, and ligating such a fragment or a mixture comprising such fragment with a DNA molecule comprising no origin of replication, e.g. a cloning vector depleted of its origin of replication, and selecting for DNA molecules replicating in at least *L. lactis* and *E. coli*.

Plasmids comprising an origin of replication of the same incompatibility group as the 2.5 Md or 5.2 Md plasmid can be identified because they cannot be maintained together with the 2.5 Md or 5.2 Md plasmid, respectively, within the same cell.

The invention concerns also the use of a DNA molecule or a recombinant DNA molecule of the invention for the preparation of hybrid vectors for the expression of a structural gene. Examples of such structural genes are given hereinbefore. The hybrid vectors can be prepared according to conventional methods using enzymes such as restriction enzymes, DNA polymerases, DNA ligases and the like.

Example 4 and 5 describe exemplary in more detail the preparation of hybrid vectors for the expression of a structural gene in lactic acid bacteria, particularly in *L. lactis*, or in Bacillus spec., particularly *B. thuringiensis*.

Transformed hosts and process for the preparation thereof

The invention concerns further a bacterial host transformed with a hybrid vector of the invention.

Transformed bacterial hosts according to the invention are suitable for the cloning, amplification and/or preparation of a hybrid vector comprising a DNA molecule defined in of a) to e). The hybrid vectors can replicate in such hosts and are not lost under selective pressure in the cell population during proliferation. The host which can be used depends on the origin of replication comprised in the hybrid vector. In the case that the hybrid vector comprises a DNA sequence with origin of replication function according to e), a suitable host is, for example, any strain of *E. coli*, Bacillus spec. or Lactococcus spec. which does not contain a plasmid with an origin of replication of the same incompatibility group.

In the case that the hybrid vector comprises a homologous or heterologous structural gene fused in a proper reading frame with the DNA sequence coding for the MSP signal peptide, a transformed host of the invention is such which is suitable for the production of a secreted homologous or heterologous protein, e.g. a strain of *L. lactis*.

An example for a transformed host according to the invention is an *E. coli* strain, e.g. TG1, C600 or HB101 transformed with pUCRS, pSC12, pSC12ΔP, pSC12ΔN, pSC12ΔNP, pSC18, pSC18ΔN, pSC18ΔP, pVAHIR, pVAHIR-1, pSC12HIR, pSC12HIR-1, or pSC12HIRTerm, or *L. cremoris*, or a plasmid-free *L. lactis*, e.g. *L. lactis* LM0230, or a Bacillus strain, e.g. *B. thufingiensis*, transformed with either of these plasmidso Preferred are *E. coli* TG1 transformed with pUCRS, *L. lactis* transformed with pUCRS, pSC12HIRTerm, pSC12 or pSC18, and *B. thuringiensis* transformed with pVAHIR or pVAHIR-1.

The invention concerns also a method for the preparation of such transformants comprising treatment of a host under transforming conditions with a recombinant DNA molecule of the present invention, especially a hybrid vector of the invention, optionally together with a selection marker gene and selecting the transformants.

Process for the preparation of polypeptides

The invention concerns further a method for the preparation of a polypeptide, characterized in that a homologous or heterologous structural gene is fused in proper reading frame with the DNA sequence coding for the MSP signal peptide, that a suitable host such as a gram positive bacterial host, for example a lactococcal host, e.g. *L. lactis* LM0230, or Bacillus spec. e.g. *B. thuringiensis*, is transformed with a hybrid vector comprising such fused gene and that the polypeptide encoded by said gene is secreted from the host cells. When required, the polypeptide is isolated from the supernatant according to conventional methods. In a preferred embodiment of the invention a bacterial host is used which does not secrete a protease in its culture medium which degrades the expressed protein.

Such a preferred embodiment of the invention is, for example, the production of proteins, e.g. desulfatohirudin, which are secreted from *L. lactis* LM0230 cells transformed with a hybrid vector of the invention comprising a gene encoding such protein, e.g. pSC12HIR, pSC12HIR-1 or in particular pSC12HIRTenn. Concentrations of active desulfatohirudin can be obtained from supernatant of stationary phase cultures of *L. lactis* LM0230 cells transformed with pSC12HIR or pSC12HIR-1. In the supernatant of *L. lactis* LM0230 cells transformed with pSC12HIRTerm the yield in desulfatohirudin is increased. Surprisingly, the levels of heterologous gene products, e.g. desulfatohirudin, do not decrease after prolonged incubation, e.g. over night, of the stationary phase cultures indicating absence of proteolytic degradation of the heterologous gene products in the supernatant.

In another embodiment of the invention the cells may be collected from the nutrient medium either in the log phase or in the stationary phase of the culture, e.g. by centrifugation or filtration, and resuspended in a smaller volume, e.g. in about 1% up to 20% of the original culture volume, of fresh nutrient medium or suitable buffer solution. Incubation of the resuspended cells results in an increased yield of heterologous gene product which is secreted into the supernatant. For example, in a culture of L. lactis LM0230 transformed with pSC12HIR an increased yield in desulfatohirudin can be obtained in the supernatant if the cells of a stationary phase culture are collected by centrifugation, resuspended in about 1/10 9vol. of fresh nutrient medium and incubated for about 30 rain at about 30° C.

Another embodiment of the invention is the production of MSP which is secreted from a gram positive host cell transformed with a hybrid vector of the invention, e.g. pUCRS, according to the methods described above.

A further embodiment of the invention is the production of desulfatohirudin in B. thuringiensis, preferentially in strain HD1 cryB (DSM 4574), transformed with pVAHIR or pVAHIR- 1.

SHORT DESCRIPTION OF THE FIGURES

FIG. 1: Physical map of plasmid pUC838. The map positions are approximate and given in kbp. The pUC 18 mojety extends from map position 0 up to 2.7 and the pVA838 mojety carrying the erythromycin resistance gene extends from map position 2.7 up to 4.4. The restriction sites shown in brackets were destroyed during the preparation of the recombinant molecule. The meanings of the abbreviations are: $amp^r$, ampicillin resistance gene; $ery^r$, erythromycin resistance gene; $ori_{puc}$, origin of replication derived from pUC 18.

FIG. 2: Physical map of plasmid pSC12. The map positions are approximate and are given in kbp. pUC18 DNA extends from position 0 up to 2.7. The 1.7 kb erythromycin resistance carrying fragment of pVA838 extends from position 2.7 up to 4.4. The *L. lactis* 2.5 Md plasmid derived insert extends from position 4.4 up to 8.0/0. The restriction sites shown in brackets were destroyed during the preparation of the recombinant molecules. The meanings of the abbreviations are: PL1, pUC polylinker region from the EcoRI to the (SmaI) site, PL2, pUC polylinker region from the (SmaI) to the SphI site; $amp^r$, ampicillin resistance gene; $ery^r$, erythromycin resistance gene; $ori_{puc}$, origin of replication derived from pUC; $ori_{11}$, origin of replication derived from lactococcal 2.5 Md plasmid as conducted from deletion analysis.

FIG. 3: Physical map of plasmid pSC18. The map positions are approximate and are given in kbp. pUC18 DNA extends from position 0 up to 2.7. The 1.7 kb erythromycin resistance carrying fragment of pVA838 extends from position 2.7 up to 4.4. The *L. lactis* 5.2 Md plasmid derived insert extends from position 4.4 up to 8.5/0. The restriction sites shown in brackets were destroyed during the preparation of the recombinant molecules. The meanings of the abbreviations are: PL1, pUC polylinker region from the EcoRI to the (SmaI) site; PL2, pUC polylinker region from the (BamHI) to the HindIII site; $amp^r$, ampicillin resistance gene; $ery^r$, erythromycin resistance gene; $ori_{puc}$, origin of replication derived from pUC; $ori_{12}$, origin of replication derived from lactococcal 5.2 Md plasmid as conducted from deletion analysis.

| Abbreviations | |
|---|---|
| dNTP | deoxy nucleotide trisphosphate |
| HPLC | high performance liquid chromatography |
| IPTG | isopropyl-β-D-thiogalactopyranoside |
| kbp | kilo base pairs |
| kD | kilo Daltons |
| LB | Luria broth nutrient medium (Gibco/BRL) |
| Md | Mega Daltons |
| sCD23 | soluble CD23, i.e. 25 k IgE-binding factor |
| SLPI | Secretory Leucoproteinase Inhibitor |

The following examples serve to illustrate present invention, however, they should not be construed as a limitation thereof.

Material and Methods

Strains

*L. lactis* LM0230 is a plasmidfree derivative of *L. lactis* C2 (Efstathiou J. D. and L. L McKay, 1977). It is deposited with the Deutsche Sammlung von Mikroorganismen und Zellkulturen (see hereinafter).

*L. lactis* C2 (NCDO 2031 ), and *L. lactis* LL712 which latter serve as the source of the 2.5 Md and 5.2 Md plasmids, are closely related or identical (F. L. Davis et al., 1981). The former is obtainable, for example, from the National Collection of Diary Organisms, UK (NCDO 2031 ), the latter is deposited with the Deutsche Sammlung von Mikcroorganismen und Zellkulturen (see hereinafter).

*E. coli* TG1 has the genotype K12, Δ(lac-pro), supE, thi, hsdD5/F'traD36, $proA^+B^+$, $lacI^q$, lacZΔM15 and is obtainable from Amersham; it is described in the manual "Oligonucleotide-directed in vitro mutagenesis system" of Amersham.

General Methods

Transformation

*E. coli* is transformed according to the calcium chloride method as described in Maniatis et al. (1982).

Transformation of lactococcal strains is performed by electroporation using a Gene Pulser® apparatus from BioRad and following their protocol for *L. lactis* LM0230.

Plasmid Preparation

Plasmid DNA from *E. coli* is prepared according to the method of Birnboim and Doly (1979).

The same method is used for the isolation of plasmids from lactococci with the following modifications:

a) Overnight cultures are grown in M17-G medium (Terzaghi and Sadine, 1975) at 30° C., diluted 1:10 into fresh medium and grown for another two hours.

b) Incubation with lysozyme is performed also in the presence of mutanolysin (50 mg/l) for 10–20 min at 37° C.

A plasmid pool from *L. lactis* LL712 is prepared by the same method and the plasmid fraction is further purified by CsCl-ethidium bromide equilibrium centrifugation (Clewell and Helinski, 1969). The three smaller plasmids (1.8 Md, 2.5 Md, 5.2 Md; Gasson, 1983) are enriched in the purified plasmid fraction while the two larger plasmids (9 Md and 33 Md; Gasson, 1983) are present in smaller quantities.

EXAMPLES

1. Construction of Shuttle Vectors for Lactic Acid Bacteria and *E. coli*

1.1 Construction of pUC838 pVA838 (ATCC 37160; Macrina et al., 1982) is a lactococcal plasmid which carries the gene for constitutively expressed erythromycin resistance on a 1.7 kbp AvaI/HindIII restriction fragment. About 10 µg of pVA838 DNA is digested with AvaI and HinIII. The ends of the DNA fragments am blunt ended with Kleenow enzyme in the presence of all four dNTPs. The fragments are separated on an agarose gel and the 1.7 kbp AvaI/HindIII fragment is recovered from the gel by electroelution.

About 200 ng of said fragment and 100 ng of SmaI-cut pUC18 (Norrander et al.) are ligated in the presence of T4-1ligase as suggested by Rusche et al. and the ligation mixture is used to transform E. coli TG 1. White colonies are picked from LB agar plates containing X-Gal, IPTG and 100 mg/l of ampicillin. Correct clones are identified by isolating and analyzing their plasmid DNA, and by their ability to grow on LB agar plates containing erythromycin (100 mg/l). The resulting plasmid is designated pUC838. The restriction sites and characteristics of pUC838 are given in FIG. 1.

1.2 Construction of pSC12

The plasmids in the pool isolated from L. lactis LL712 are separated on a preparative agarose gel. The second DNA band from bottom corresponds to the ccc form of the 2.5 Md plasmid. It is cut out and the plasmid is electroeluted. Digestion of this plasmid with SphI and agarose gel electrophoresis reveales a single 3.5 kbp fragment indicating the presence of a single or several closely spaced SphI cleavage sites in the 2.5 Md plasmid.

pUC838 is cut at its unique SphI site and treated with calf intestinal phosphatase. About 50 ng of phosphatase treated vector and 150 ng of the 3.5 kbp SphI fragment of the 2.5 Md plasmid is ligated with T4 ligase and the ligation mixture is used to transform competent E. coli TG1 cells. The transformation mixture is grown at 37° C. in 1 ml of LB for 90 min and then transferred to 200 ml of LB containing 100 mg/l of erythromycin and grown at 37° C. over night. Plasmid DNA is prepared from the cells of this culture and about 2 µg are used to transform L. lactis LM0230. Transformed L. lactis LM0230 cells are selected at 30° C. on M-17G agar plates containing 5 mg/l of erythromycin.

Plasmid DNA is isolated from several clones of the transformed L. lactis LM0230 cells and subjected to restriction enzyme analysis. All transformants investigated contained a 8.0 kbp plasmid, pSC12, from which the 3.5 kbp SphI insert can be recovered. A physical map of pSC12 is given in FIG. 2.

pSC12 is shuttled several times between L. lactis and E. coli without any obvious changes in restriction pattern.

1.3 Construction of pSC18

Plasmid pool DNA from L. lactis LL712 is partially restricted with Sau3AI by incubating 500 ng alicluots of DNA with different amounts of restriction enzyme, Samples containing partially cut DNA are identified on an agarose gel, This DNA is ligated to pUC838 vector which is previously cut at its unique BamHI site and treated with calf intestinal phosphatase.

Transformation of E. coli TG1 plasmid isolation and subsequent transformation of L. lactis LM0230 is done as described for pSC12. Again, restriction digests are performed on plasmid DNA isolated from several clones of L. lactis LM0230 transformants. They carry a 8.8 kbp plasmid, pSC18. Shuttling the plasmid several times between L. lactis and E. coli didn't result in any changes in restriction pattern indicating stability of the construct in both cell types. A physical map of pSC18 is given in FIG. 3.

2. Identification of Lactococcal origins of replication 2.1 Deletion Analysis of pSC12 and pSC18

The regions on plasmids pSC12 and pSC18 carrying the lactococcus derived origins of replication are defined by deletion analysis as follows:

DNA between appropriate restriction sites is deleted by cutting the plasmids with the corresponding restriction enzyme and recircularization with T4 ligase. The approximate location of the restriction enzyme cleavage sites in pSC12 and pSC18 are given in FIGS. 2 and 3, respectively, and in Table 1.

pSC12ΔP and pSC18ΔP are constructed by deleting the DNA between the two PvuII sites in the pUC18 part of the plasmids pSC12 and pSC18, respectively, thus removing the col E1 derived origins of replication.

In pSC12ΔN and pSC18ΔN the smaller NdeI-fragment of pSC12 or pSC18, respectively, is removed.

pSC12ΔR lacks an EcoRV fragment in the lactococcal DNA of pSC12.

In pSC12ΔNP DNA between the PvuII site in pUC and the NdeI site in the lactococcal part of pSC12 is removed. In this case the vector DNA is blunted with Kleenow enzyme before religation.

A further derivative of pSC18, pSC18ΔH, lacks DNA spanning the HindIII sites in the plasmid.

All the mutated plasmid DNAs are first isolated from E. coli TG1 transformants that are resistant to erythromycin. It is then tested whether they can be used to transform L. lactis LM0230 to erythromycin resistance. Failure to do so is assumed to indicate that the lactococcal origin of replication was removed or destroyed by the deletion. When erythromycin resistant transformants are obtained, the plasmid is reisolated and its structural integrity reconfirmed by restriction analysis.

For both the 2.5 Md and the 5.2 Md plasmid a region required for replication in streptococcus is identified. From the fact that the ΔP-derivatives could replicate in E. coli it is obvious that the cloned lactococcal origins can also function in the gram-negative E. coli bacteria.

Results of these experiments are given in Table 1.

TABLE 1

Results of the deletion analysis of pSC12 and pSC18

| Plasmid | Deleted region[1] | Deleted fragment[2] | Replication of the plasmid in | |
|---|---|---|---|---|
| | | | E. coli | L. lactis |
| pSC12 | none | | + | + |
| pSC12ΔP | PvuII (0.1), PvuII (2.5) | 2.4 | + | + |
| pSC12ΔN | NdeI (0.2), NdeI (6.2) | 2.0 | + | + |
| pSC12ΔR | EcoRV (5.0), EcoRV (7.5) | 2.5 | + | − |
| pSC12ΔNP | NdeI (6.2), PvuII (2.5) | 4.3 | ND[3] | + |
| pSC18 | none | | + | + |
| pSC18ΔP | PvuII (0.1), PvuII (2.5) | 2.4 | + | + |
| pSC18ΔN | NdeI (0.2), NdeI (7.5) | 1.2 | + | + |
| pSC18ΔH | HindIII (0), HindIII (6.5) | 2.0 | + | − |

[1]The deletions extend between two restriction sites. The approximate positions of the restriction sites in pSC12 or pSC18 are given in the brackets as the distances from the HindIII site in the pUC838-derived mojety of the plasmids which is defined as position (0). They relate to the base positions given in FIGS. 2 and 3, respectively.
[2]Approximate length of the deleted fragment in kbp.
[3]Not determined.

2.2 Source of the lactococcal origins of replication

The origin of replication in pSC12 is derived from the 2.5 Md plasmid of L. lactis LL712 as is clear from the isolation protocol for the DNA fragment carrying the origin.

The restriction enzyme cleavage pattern indicates that the origin of replication in pSC18 stems from the 5.2 Md plasmid.

2.3 Replication of pSC12 and pSC18 in other Lactic Lactococci

Strains of L. lactis, L. lactis diacetylactis and L. cremoris are successfully transformed with both plasmids. The plasmids remain stably associated with the cell population under selective pressure.

3. Cloning of the Gene encoding the Major Secretion Product (MSp) of L. lactis LM 0230

3.1. Isolation of the Maior Secreted Protein (MSP) of L. lactis LM 0230

1.5 l of an overnight culture of L. lactis LM 0230, grown at 30° C. in M- 17G, is centrifuged in a Sorvall GS-3 rotor at 7000 rpm for 20 rain at 4° C. The supernatant is collected and proteins precipitated by adding an equal volume of ice cold 10% trichloroacetic acid and incubating for 30 min at room temperature. The precipitate is collected by centrifugation in a Sorvall CS-3 rotor at 8 000 rpm and 4° C. for 30 min. The protein pellets are drained and redissolved in 3 ml of SDS-sample buffer (Laemmli, 1970). The sample is neutralized by adding a small amount of 4N NaOH and then dialyzed for 4 h against 4l of 25 mM Tris-HCl pH 6.8, 0.02% SDS. The sample recovered has a volume of about 4 ml. 3×conc. SDS-sample buffer is added to the sample in order to enlarge the volume to 6 ml.

Proteins are separated by running 2 ml aliquots on preparative 8% SDS polyacrylamide gels (Laemmli, 1970) using a Protean cell from BioRad. Small strips are cut alongside from the gel, stained with Coomassie Brilliant Blue and alestained in an aqueous solution containing 10% of Methanol and 10% of Acetic acid. They serve as markers to identify and cut out the major protein band with an apparent molecular weight of about 56 kD which is cut out of the gel.

The MSP protein is recovered from the gel by electroelution at 150 V for 2 h using a Biotrap apparatus and a buffer containing 20 mM ammonium acetate and 0.01% SDS. The eluate is dialyzed for 48 h against two changes of 20 mM ammonium acetate, 0.005% SDS. A sample of the dialyzed protein is run on a 8% SDS-PAGE and a single sharp protein band is observed with an apparent molecular weight of about 56 kD.

3.2 Analysis of the amino-terminal Sequence of MSP

Amino-terminal sequencing of the isolated MSP protein is performed according to conventional methods using a gas phase sequenator (Applied Biosystems Inc., Model 470A) with HPLC quantitation of phenylthiohydantoin-derivatives of cleaved amino acid residues.

The 28 amino acid long sequence obtained is X-X-Asn-Ser-Asp-Ile-Ala-Lys-Gln-Asp-Ala-Thr-Ile-Ser-X-Ala-Gln-Ser-Ala-Lys-Ala-Gln-Ala-Gln-Ala-Cln-Val-Asp. The first two amino acids and the amino acid in position 15 which are indicated with "X" are not determined.

3.3 Synthesis of a mixed Oligonucleotide Probe

Based on the amino acid sequence Asp-Ile-Ala-Lys-Gln-Asp-Ala-Thr-Ile, which corresponds to the amino acids in position 5 to 13 in the N-terminus sequence of MSP, a mixed oligonucleotide is designed and constructed for the screening of a DNA library. Inosine is inserted at the two positions in the 23-mer where the degeneracy of the genetic code would require all 4 dNTPs in order to decrease the complexity of the probe. The nucleotide sequence of the oligonucleotide mixture is $GAN_1$ $ATN_2$ GCI $AAN_3$ $CAN_3$ $GAN_1$ GCI AC. $N_1$ is T or C; $N_2$ is T, C or A; $N_3$ is A or G. A represents a nucleotide with the base Adenine, T with Thymine, C with Cytidine, G with Guanosine and I with Inosine.

3.4. Construction of a Genomic Library of L. lactis LM 0230

Chromosomal DNA is isolated from L. lactis LM 0230 by a modification of the protocol used for plasmid isolation: after treatment with lysozyme and mutanolysin the cells are incubated for two hours at 56° C. with proteinase K (100 mg/l) in 10 mM Tris-HCl pH 8, 20 mM EDTA, 0.5% SDS. The DNA is extracted once with phenol/chloroform (1 vol:1 vol) and then purified by CsCl density gradient centrifugation.

Chromosomal DNA is partially digested with Sau3AI and size fractionated on sucrose gradients as described in Maniatis. Fragments between about 10–20 kbp are collected.

λEMBL 3 DNA is cleaved with BamHI and EcoRI and purified by phenol extraction and ethanol precipitation. It is then ligated with the 10–20 kbp fragments in the presence of hexamminecobalt(III)chloride to favour the formation of concatamers. (Rusche J. R. et al., 1985). The ligation mixture is packaged in vitro using the Gigapack Plus® system from Stratagene.

Recombinants are selected by plating the library on E. coli Q 359 (Kahn J. et al., 1980). A total of about 600 000 recombinant phages is obtained.

3.5 Screening the Library for DNA sequences encoding MSP

About 15 000 recombinant λ EMBL 3 plaques are plated per petri dish (15 cm diameter) and transferred to Plaque-Screen® membranes (NEN). The filters are screened by hybridization with the mixed oligonucleotide probe described in Example 3.3 which was labeled with $[\gamma^{32}P]ATP$ using T4 Kinase according to standard procedures described in Maniatis et al. (1982).

Positive plaques are identified and subjected to a second round of screening at low plaque density.

DNA is prepared from positive phages, digested with restriction enzymes and subjected to Southern analysis as described in Maniatis. Southern blots are probed with the mixed oligonucleotide. It hybridizes to a 3.5 kbp EcoRI/SalI fragment in the L. lactis insert of a positive phage. Further probing showed a 2.1 kbp HindIII fragment within the 3.5 kbp EcoRI/SalI fragment to hybridize with the oligonucleotide mixture.

The approximate distances of different restriction sites from the EcoRI cut end of the 3.5 kbp EcoRI/SalI fragment are determined by agarose gel electrophoresis after digestion of the fragment with the respective enzymes and suitable enzyme mixtures. The EcoRI cut end is located about 0.5 kbp away from a HindIII site, about 2.6 kbp from a second HindIII site, and about 3.15 kbp from a third HindIII site.

3.6 Construction of pUCRS

DNA from a positive phage is digested with EcoRI and SalI. The DNA fragments are separated on an 0.6% agarose gel and the 3.5 kbp EcoRI/SalI fragment is cut out and isolated by electroelution. A three fold molar excess of this fragment is ligated to pUC19 which is cut with EcoRI and SalI and treated with alkaline phosphatase.

The ligation mixture is used to transform E. coli TG1 and transformants are selected on plates containing 100 mg/l of ampicillin. Plasmid DNA is prepared from transformants and restriction analyses is performed to identify the correct construct which is designated pUCRS.

E. coli TG1 transformed with pUCRS is deposited with the Deutsche Sammlung von Mikroorganismen und Zellkulturen (DSM).

3.7. Sequencing the gene for the Major Secretion Product (MSP)

Sequencing is done by the chain termination method (Sanger F. et al., 1977) using Sequenase® from USB C.

The 3.5 kbp EcoRI/SalI fragment prepared as described in Example 3.6 is subcloned into M13 mp18. The resulting plasmid is named M13 mp18RS. The 2.1 kbp HindIII fragment of the 3.5 kbp EcoRI/SalI fragment is cloned into M13 mp19, the resulting plasmid is M13 mp19H. A set of unidirectional deletions is generated from the SalI end of the insert in M13 mp18RS by digesting the DNA with exonucleaseIII and SI (Henikoff, 1984; Yanisch-Perron et al., 1985). The deletions extend about 2 kbp into the insert. Sequencing these deletions from the universal mp18 primer yielded the sequence information for one strand. Based on this sequence, a set of synthetic oligonucleotides is synthesized and serves as primers to sequence the second strand. Additional sequence information is gained by sequencing exoIII-S 1 deletions generated from M13 mp19H with the same method. The DNA sequence of a 1920 bp fragment of the 3.5 kbp EcoRI/SalI fragment is depicted in the sequence listing under SEQ ID No. 1. It comprises part of the MSP promoter region, the DNA sequence encoding the MSP signal peptide and the structural gene for mature MSP.

Analysis of the about 2 kbp long DNA sequence revealed the presence of a single open reading frame (ORF) coding for a protein having 461 amino acid residues. Comparison of the deduced amino acid sequence with the data obtained from sequencing the N-terminus of the isolated MSP identified a mature form of the protein with 434 amino acids which is preceded in frame by 27 amino acids. The peptide formed by the latter amino acids has the structure of a typical signal peptide. Charged residues are found at the N-terminus while the rest of the sequence consists mainly of hydrophobic amino acids. The amino acid composition around the cleavage site follows the rules deduced from other signal peptides (Von Heijne, 1983).

4. Production of recombinant Desulfatohirudin in *Lactococcus lactis*

4.1 Construction of Desulfatohirudin Secretion Plasmids

Plasmid M13 mp19H contains a 2.1 kbp HindIII fragment encoding the N-terminus half of MSP including the signal peptide and about 1.5 kbp of upstream DNA. This plasmid is cleaved at its unique ScaI site 129 bp downstream of the COOH-terminus of the signal peptide. A blunt ended 211 bp DNA fragment encoding the genetic information for desulfatohirudin is isolated from plasmid pML310 (published in the European Patent Application EP-A-168 342) and inserted at the cleaved ScaI site of M13 mp19H. An in frame fusion between the DNA sequence encoding the MSP signal peptide and the desulfatohirudin structural gene is created by removing the excess DNA separating the codon for the last amino acid of the signal peptide (Ala) and the codon for the first amino acid of desulfatohirudin (Val). This is achieved by oligonucleotide-directed in vitro mutagenesis using the system from Amersham. The 29 bp oligonucleotide comprises the last 14 bp of the signal peptide and the first 15 bp of the hirudin gene. The sequence of the resulting fusion is depicted in the sequence listing under SEQ ID No. 2.

The HindIII fragment carrying the fusion is cut out and inserted into the unique HindIII of pSC12. Both orientations of the insert are recovered. The resulting plasmids are named pSC12HIR and pSC12HIR-1, respectively.

Another plasmid (pSC12HIRTenn) is constructed by inserting the trpA transcription terminator of *E. coli* (Pharmacia) at the unique HpaI site of pSC12HIR about 125 bp downstream of the desulfatohirudin gene.

4.2 Secretion of Desulfatohirudin by *L. lactis*

The desulfatohirudin fusion plasmids are transformed into *L. lactis* LM 0230Transformants are grown in M-17G medium supplemented with 2 % of glucose in the presence of erythromycin (5 mg/l) at 30° C. When the cultures reach stationary phase, 1.5 ml samples are centrifuged in an Eppendorf® tube. The culture supernatants are removed and frozen at −70° C. The cultures are then further grown overnight before a second sample is taken, centrifuged, the supernatant removed and also frozen. The production of secreted desulfatohirudin is determined with a bioassay.

The bioassay measures the thrombin inhibition activity of desulfatohirudin in the supernatants collected. A detailed protocol of the bioassay, which is a thrombin inhibition assay is presented hereinafter:

The buffer used for making all dilutions of samples and reagents is 0.2M Tris-HCl, pH 7.5 containing 1.0M NaCl and 0.01% bovine serum albumin. Thrombin is from human plasma (Protogen AG, Läufelfingen, product No. 80-13-1102), the chromogenic thrombin substrate is Chromozyme TH (Boehringer, Mannheim, product No 206849). The p-nitroaniline released from Chromozym TH is measured with a Dynatech MR 600 microplate reader. All assays are performed in microtiter plates (Nunc, MicroWell plates). Each well receives: 50 µl buffer, 50 µl supernatant with unknown concentration of thrombin inhibitory activity, i.e. desulfatohirudin, and 25 µl thrombin solution. The reaction is started by adding 150 µl substrate solution (330 µg/ml) and the plates are incubated for two hours at 37° C. The concentration of thrombin is adjusted to give an $A_{405}nm=0.8\pm0.2$ in an uninhibited control well. Both substrate and thrombin solutions are kept frozen at −20° C. and are thawed immediately before being used. A standard curve with known concentrations of a r[$Tyr^{63}$]desulfatohirudin (40, 20, 10, 5, 2.5 and 1.25 ng/ml) is used to convert the OD-measurements into the concentrations of active desulfatohirudin.

In the supernatant of stationary phase cultures of *L. lactis* LM0230 cells transformed with either pSC12HIR or pSC12HIR-1 the same level of desulfatohirudin activity is determined. In the supernatant of a stationary phase culture of *L. lactis* LM0230 cells transformed with pSC12HIRTerm, the level of desulfatohirudin activity is increased by about 50%. Supernatants of cells transformed as a control with pSC12 contain no desulfatohirudin activity.

The levels of desulfatohirudin in the supernatant did not decrease after prolonged incubation for about 16 h of the stationary phase cultures. These results indicate the absence of proteolytic degradation in the supernatant of *L. lactis* LM0230.

In one experiment, cells are first collected by centrifugation and then resuspended in $\frac{1}{10}$ volume of fresh medium and incubating at 30° C. for 30 min expression period. Bioassay measures an about six fold higher level of desulfatohirudin activity than in the experiments described hereinabove. In a more sophisticated form, concentration of the cells for an expression period is a way to increase the concentration of secreted product in the supernatant.

5. Production of recombinant Desulfatohirudin in *Bacillus thuringiensis*

5.1 Construction of plasmid pVAHIR

Plasmid pVA838 (Macrina et al, 1982) is digested with HindHi and the 5.0 kbp fragment carrying the gene for erythromycin resistance and the gram positive origin of replication is isolated from a 0.5 % agarose gel by electroelution.

The HindIII fragment containing the desulfatohirudin gene is isolated in a similar manner from pSC12HIR.

The two fragments are ligated in the presence of T4-ligase and the ligation mixture is directly used to transform *L. lactis* LM 0230 by electroporation. Erythromycin resistant transformants are selected and plasmid DNA is prepared from them.

Restriction analyses of these plasmids is performed to identify correct constructions. Both orientations of the HindIII desulfohirudin expression cassette are obtained and can be used for the production of Desulfatohirudin in Bacillus thuringiensis. The plasmids are named pVAHIR and pVAHIR-1.

5.2 Secretion of Desulfatohirudin by *B. thuringiensis*

*B. thuringiensis* strain HD1 cryB (DSM 4574) is transformed with pVAHIR using electroporation (W. Schurter et al, 1989).

Transformants are selected on LB plates containing 20 μg/ml of erythromycin at 27° C. or 30° C. Plasmid DNA is prepared from individual transformants by the same method as used for *L. lactis*. Restriction analyses reconfirms that the structure of the isolated plasmids is identical to pVAHIR.

Transformants harbouring pVAHIR or pVA838—as a control—are grown in LB containing 20 mg/l of erythromycin at 27° C. over night. The cultures are diluted 1:200 into fresh medium and grown further at 30° C. The cultures are centrifuged and the supernatants are assayed for desulfohirudin activity 7 h after dilution.

Desulfatohirudin is detected in the supernatant of cells transformed with pVAHIR, while none is measured in the control with pVA838.

Deposited Microorganisms

The following microorganisms are deposited according to the Budapest Treaty with the Deutsche Sammlung von Mikroorganismen und Zellkulturen (DSM), Mascheroder Weg 1b, D-3300 Braunschweig:

| Microorganism | Deposition No. | Date of deposition |
| --- | --- | --- |
| *E. coli* K12 TG1/pUCRS | DSM 5803 | February 16, 1990 |
| *Lactococcus lactis* LL712 | DSM 5804 | February 16, 1990 |
| *Lactococcus lactis* LM0230 | DSM 5805 | February 16, 1990 |

References

Bates, E. E. M. et al. (1989) Applied and Environmental Microbiology 55, 2095.
Bernton, W. D., and Davis, R. W. (1977), Science 196 180.
Birnboim, H. C. and Doly, J. (1979) Nucleic Acids Res., 7, 1513.
Botstein, D. and Shortle, D. (1985) Science 229, 1193.
Chassy, B. M. (1987) FEMS Microbiol. Rev. 46, 297.
Clewell, D. and Helinski, D. R. (1969) Proc. Natl. Acad. Sci. USA, 62, 1159.
Davies, F.L., Underwood, H. M. and Gasson, J. M. ( 1981 ) J. of Applied Bacteriology, 51, 325.
De Vos, W. M. (1987) FEMS Microbiol. Rev. 46, 281.
Efstathiou, J. D. and McKay, L. L. (1977) J. Bacteriol., 130, 257.
Gasson, J. M. (1983) J. Bacteriol., 154, 1.
Gasson, J. M. and Anderson P.H. (1985) FEMS Microbiol. Lett., 30, 193.
Henikoff, S. (1984) Gene, 28,351.
Jos, M. (1985) Applied and Environmental Microbiology 50, 540.
Karn, J., Brenner, S., Barnett, L., and Cesareni, G. (1980) Proc. Natl. Acad. Sci. USA, 77, 5172.
Laemmli, U. K. (1970) Nature, 227,680.
Macrina, F. L. et al., in Genetic Engineering of Microorganisms for Chemicals, Plenum Press, New York, (1982).
Maniatis, T., Fritsch, E. F. and Sambrook, J. (1982) Molecular cloning, a Laboratory Manual. Cold Spring Harbor Laboratory, New York.
Norrander, J. et al. (1983) Gene, 26, 101.
Norris, K. et al. (1983) Nucl. Acids Res. 11, 5103.
Powell et al. (1988) Applied and Environmental Microbiology 54, 6.
Oto, R. et al. (1982) Applied and Environmental Microbiology 43, 1272.
Rusche, L. R. and Howards-Flanders, P. (1985) Nucleic Acids Res., 13, 1997.
Sanger, F. Milken, S., Coulson, A. R. (1977) Proc. Natl. Acad. Sci. USA, 74, 5463.
Schurter, W., Geiser, M. and Mathe, D. (1989) Mol. Gen. Genet. 218, 177.
Terzaghi, B. K. and Sadine, N. E. (1975) Applied Microbiology, 29, 807.
Von Heijne, G. (1983) Eur. J. Blochem., 133, 17.
Yanisch-Perron, C., Vieira, J. and Messing, J. (1985) Gene, 33, 103.
Zoller, M. J. and Smith, M. (1983) Methods Enzymol. 100, 468.

We claim:

1. A method for the preparation of a polypeptide comprising the steps of (a) fusing a homologous or heterologous structural gene in proper reading frame with a DNA sequence coding for a MSP signal peptide, said gene and MSP signal peptide operably linked with a suitable promoter, (b) transforming a suitable host with a hybrid vector comprising a fused gene prepared in (a), (c) secreting the polypeptide encoded by said fused gene from the host cells and, when required, (d) isolating the polypeptide from the supernatant.

2. A method according to claim 1 in which a host selected from the group of hosts consisting of Lactococcus spec. and Bacillus spec. is used.

3. A method according to claim 1 in which a bacterial host is used which does not secrete in its culture medium a protease which degrades the expressed protein.

4. A method according to claim 1 in which desulfatohirudin is produced.

5. A method according to claim 4 in L. lactis LM0230 cells transformed with pSC12HIR, pSC12HIR-1 or pSC12HIRTerm are used.

6. A method according to claim 4 in L. lactis LM0230 cells transformed pSC12HIRTerm are used.

7. A method according to claim 4 in which B. thuringiensis cells transformed with pVAHIR or pVAHIR-1 are used.

8. A method according to claim 1 characterized in that (a) the transformed cells are collected from the nutrient medium either in the log phase or in the stationary phase of the culture, (b) they are resuspended in a smaller volume of fresh nutrient medium or suitable buffer solution and (c) they are further incubated before isolating the desired product from the supernatant.

9. A method according to claim 8 characterized in that the transformed cells are resuspended in about 1% up to 20% of the original culture volume.

10. A method according to claim 9 characterized in that the L. lactis LM0230 cells transformed with pSC12HIR are resuspended in about 1/10 vol. of fresh nutrient medium and incubated for about 30 min at about 30° C.

11. A method according to claim 1 in which MSP is produced.

12. A shuttle vector comprising a promoter operably linked to a DNA sequence encoding a MSP signal peptide, said promoter and DNA sequence operably linked to a DNA molecule encoding a protein of interest.

13. The shuttle vector of claim 12, wherein said promoter is a MSP promoter.

14. The shuttle vector of claim 13, wherein said MSP promoter is the DNA sequence given in SEQ ID NO: 1.

15. The shuttle vector of claim 12, wherein said protein of interest is MSP.

16. The shuttle vector of claim 15, wherein said MSP protein has the amino acid sequence given in SEQ ID NO: 1.

17. The shuttle vector of claim 16, wherein said MSP protein is encoded by the DNA sequence given in SEQ ID NO: 1.

18. The shuttle vector of claim 12, wherein said protein of interest is hirudin.

19. The shuttle vector of claim 18, wherein said himdin has the amino acid sequence given in SEQ ID NO: 2.

20. The shuttle vector of claim 19, wherein said himdin is encoded by the DNA sequence given in SEQ ID NO: 2.

21. The shuttle vector of claim 12, wherein said MSP signal peptide comprises the amino acid sequence given in SEQ ID NO: 1.

22. The shuttle vector of claim 21, wherein said MSP signal peptide is encoded by the DNA sequence given in SEQ ID NO: 1.

23. The shuttle vector of claim 12, wherein said vector further comprises an origin of replication.

24. The shuttle vector of claim 23, wherein said origin of replication is the origin of replication of the 2.5 MD plasmid of L. Lactis LL712, the 5.2 MD plasmid of L. Lactis LL712, or a plasmid of the same incompatibility group as the 2.5 MD plasmid or the 5.2 MD plasmid of L. Lactis LL712.

25. The shuttle vector of claim 15, wherein said vector further comprises an origin of replication.

26. The shuttle vector of claim 18, wherein said shuttle vector further comprises an origin of replication.

27. The shuttle vector of claim 12, wherein said vector is selected from a group of vectors consisting of pSC12, pSC12ΔP, pSC12ΔN, pSC12ΔNP, pSC18, pSC18ΔP or pSC18ΔN, pSC12HIR, pSC12HIR-1, pSC12HIRTerm, pUCRS, M13mp18RS, M13mp19H, pVAHIR-1 and pVAHIR.

28. The shuttle vector of claim 27, wherein said shuffle vector is pSC12HIRTerm.

29. A DNA molecule comprising a MSP promoter.

30. The DNA molecule of claim 29, wherein said MSP promoter comprises the DNA sequence given in SEQ ID NO: 1.

31. The DNA molecule of claim 29, further comprising a DNA sequence encoding a signal peptide operably linked to said promoter.

32. The DNA molecule of claim 31, wherein said signal peptide is an MSP signal peptide.

33. The DNA molecule of claim 32, wherein said MSP signal peptide has the amino acid sequence given in SEQ ID NO: 1.

34. The DNA molecule of claim 33, wherein said DNA encoding such signal peptide comprises the DNA sequence given in SEQ ID NO: 1.

35. A DNA molecule comprising a DNA sequence encoding a MSP signal peptide.

36. The DNA molecule of claim 35, wherein said MSP signal peptide comprising the amino acid sequence given in SEQ ID NO: 1.

37. The DNA molecule of claim 36, wherein said DNA encoding said signal peptide comprises the DNA sequence given in SEQ ID NO: 1.

38. The DNA molecule of claim 35, operably linked to a promoter.

39. The DNA sequence of claim 38, operably linked to a protein of interest.

40. The DNA molecule of claim 39, wherein said protein of interest is MSP protein or hirudin.

41. A DNA molecule encoding MSP protein.

42. The DNA molecule of 41, wherein said MSP protein comprises the amino sequence given in SEQ ID NO: 1.

43. The DNA molecule of claim 42, wherein said DNA encoding MSP comprises the DNA sequence given in SEQ ID NO: 1.

44. A host transformed with a shuttle vector according to claim 12.

45. The transformed host of claim 44 selected from the group of transformed hosts consisting of *E. coli* strain TG1, C600, HB 101 transformed with either of the plasmids pUCRS, pSC12, pSC12ΔP, pSC12ΔN, pSC12ΔNP, pSC18, pSC18ΔN, pSC18ΔP, PSC12HIR, pSC12HIR-1, or pSC12HIRTerm, and *L. cremoris*, a plasmid-free *L. lactis* and a Bacillus strain transformed with either of pUCRS, pSC12, pSC12ΔP, pSC12ΔN, pSC12ΔNP, pSC18, pSC18ΔN, pSC18ΔP, pVAHIR, pVAHIR-1, pSC12HIR, pSC12HIR-1 or pSC12HIRTerm.

46. A host transformed with the DNA molecule of claim 29.

47. A host transformed with the DNA molecule of claim 32.

48. A host transformed with the DNA molecule of claim 35.

49. A host transformed with the DNA molecule of claim 39.

* * * * *